(12) United States Patent
Björsell et al.

(10) Patent No.: US 8,774,378 B2
(45) Date of Patent: Jul. 8, 2014

(54) ALLOCATING CHARGES FOR COMMUNICATIONS SERVICES

(71) Applicant: Digifonica (International) Limited, Vancouver (CA)

(72) Inventors: Johan Emil Viktor Björsell, Vancouver (CA); Fuad Arafa, Vancouver (CA)

(73) Assignee: Digifonica (International) Limited, Vancouver (CA)

( * ) Notice: Subject to any disclaimer, the term of this patent is extended or adjusted under 35 U.S.C. 154(b) by 0 days.

(21) Appl. No.: 14/029,615

(22) Filed: Sep. 17, 2013

(65) Prior Publication Data

US 2014/0016764 A1 Jan. 16, 2014

Related U.S. Application Data

(63) Continuation of application No. 12/513,147, filed as application No. PCT/CA2007/001956 on Nov. 1, 2007, now Pat. No. 8,542,815.

(60) Provisional application No. 60/856,212, filed on Nov. 2, 2006.

(51) Int. Cl.
*H04M 15/00* (2006.01)

(52) U.S. Cl.
USPC .................................. 379/114.2; 379/114.17

(58) Field of Classification Search
USPC ....................................... 379/114.01–121.06
See application file for complete search history.

(56) References Cited

U.S. PATENT DOCUMENTS

| | | |
|---|---|---|
| 4,916,491 A | 4/1990 | Katoh |
| 4,992,971 A | 2/1991 | Hayashi |
| 5,146,491 A | 9/1992 | Silver et al. |
| 5,247,571 A | 9/1993 | Kay et al. |
| 5,303,297 A | 4/1994 | Hillis |
| 5,359,642 A | 10/1994 | Castro |

(Continued)

FOREIGN PATENT DOCUMENTS

| | | |
|---|---|---|
| CA | 2249668 | 4/1999 |
| EP | 1 389 862 A1 | 2/2004 |

(Continued)

OTHER PUBLICATIONS

Cisco. "Lawful Intercept Requirements Summary." http://www.faqs.org/rfcs/rfc3924.html, Nov. 8, 2006.

(Continued)

*Primary Examiner* — Simon Sing
(74) *Attorney, Agent, or Firm* — Knobbe, Martens, Olson & Bear LLP

(57) ABSTRACT

A process and apparatus to facilitate communication between callers and callees in a system comprising a plurality of nodes with which callers and callees are associated is disclosed. In response to initiation of a call by a calling subscriber, a caller identifier and a callee identifier are received. Call classification criteria associated with the caller identifier are used to classify the call as a public network call or a private network call. A routing message identifying an address, on the private network, associated with the callee is produced when the call is classified as a private network call and a routing message identifying a gateway to the public network is produced when the call is classified as a public network call.

40 Claims, 32 Drawing Sheets

(56) References Cited

U.S. PATENT DOCUMENTS

| | | |
|---|---|---|
| 5,425,085 A | 6/1995 | Weinberger et al. |
| 5,440,621 A | 8/1995 | Castro |
| 5,454,030 A | 9/1995 | de Oliveira et al. |
| 5,469,497 A | 11/1995 | Pierce et al. |
| 5,506,893 A | 4/1996 | Buscher et al. |
| 5,519,769 A | 5/1996 | Weinberger et al. |
| 5,559,871 A | 9/1996 | Smith |
| 5,590,133 A | 12/1996 | Billstrom et al. |
| 5,608,786 A | 3/1997 | Gordon |
| 5,621,787 A | 4/1997 | McKoy et al. |
| 5,633,913 A | 5/1997 | Talarmo |
| 5,661,790 A | 8/1997 | Hsu |
| 5,712,907 A | 1/1998 | Wegner et al. |
| 5,719,926 A * | 2/1998 | Hill .................. 379/115.02 |
| 5,722,067 A * | 2/1998 | Fougnies et al. ......... 455/406 |
| 5,724,355 A | 3/1998 | Bruno et al. |
| 5,726,984 A | 3/1998 | Kubler et al. |
| 5,737,414 A | 4/1998 | Walker et al. |
| 5,751,961 A | 5/1998 | Smyk |
| 5,793,762 A | 8/1998 | Penners et al. |
| 5,799,072 A | 8/1998 | Vulcan et al. |
| 5,802,502 A | 9/1998 | Gell et al. |
| 5,825,863 A | 10/1998 | Walker |
| 5,828,740 A | 10/1998 | Khuc et al. |
| 5,838,682 A | 11/1998 | Dekelbaum et al. |
| 5,845,267 A | 12/1998 | Ronen |
| 5,850,433 A | 12/1998 | Rondeau |
| 5,864,610 A | 1/1999 | Ronen |
| 5,867,495 A | 2/1999 | Elliott et al. |
| 5,883,891 A | 3/1999 | Williams et al. |
| 5,889,774 A | 3/1999 | Mirashrafi et al. |
| 5,905,736 A | 5/1999 | Ronen et al. |
| 5,907,547 A | 5/1999 | Foladare et al. |
| 5,910,946 A | 6/1999 | Csapo |
| 5,915,005 A | 6/1999 | He |
| 5,915,093 A * | 6/1999 | Berlin et al. .................. 709/219 |
| 5,923,659 A | 7/1999 | Curry et al. |
| 5,930,343 A | 7/1999 | Vasquez |
| 5,937,045 A | 8/1999 | Yaoya et al. |
| 5,940,598 A | 8/1999 | Strauss et al. |
| 5,953,504 A | 9/1999 | Sokal et al. |
| 5,956,391 A | 9/1999 | Melen et al. |
| 5,970,477 A | 10/1999 | Roden |
| 5,974,043 A | 10/1999 | Solomon |
| 5,991,291 A | 11/1999 | Asai et al. |
| 6,005,926 A | 12/1999 | Mashinsky |
| 6,014,379 A | 1/2000 | White et al. |
| 6,021,126 A | 2/2000 | White et al. |
| 6,029,062 A * | 2/2000 | Hanson ................. 455/408 |
| 6,052,445 A | 4/2000 | Bashoura et al. |
| 6,058,300 A | 5/2000 | Hanson |
| 6,069,890 A | 5/2000 | White et al. |
| 6,073,013 A | 6/2000 | Agre et al. |
| 6,078,647 A | 6/2000 | D'Eletto |
| 6,104,704 A | 8/2000 | Buhler et al. |
| 6,104,711 A | 8/2000 | Voit |
| 6,115,737 A | 9/2000 | Ely et al. |
| 6,128,304 A | 10/2000 | Gardell et al. |
| 6,137,869 A | 10/2000 | Voit et al. |
| 6,141,404 A | 10/2000 | Westerlage et al. |
| 6,151,385 A | 11/2000 | Reich et al. |
| 6,188,752 B1 | 2/2001 | Lesley |
| 6,249,573 B1 * | 6/2001 | Hudson ................. 379/114.2 |
| 6,282,517 B1 | 8/2001 | Voit |
| 6,298,062 B1 | 10/2001 | Gardell et al. |
| 6,351,464 B1 | 2/2002 | Galvin et al. |
| 6,359,880 B1 | 3/2002 | Curry et al. |
| 6,430,275 B1 | 8/2002 | Voit et al. |
| 6,507,644 B1 | 1/2003 | Henderson et al. |
| 6,597,686 B1 | 7/2003 | Smyk |
| 6,674,745 B1 | 1/2004 | Schuster et al. |
| 6,724,860 B2 | 4/2004 | Stumer et al. |
| 6,744,858 B1 | 6/2004 | Ryan et al. |
| 6,766,159 B2 | 7/2004 | Lindholm |
| 6,798,767 B1 | 9/2004 | Alexander et al. |
| 6,819,929 B2 | 11/2004 | Antonucci et al. |
| 6,954,453 B1 | 10/2005 | Schindler |
| 6,963,557 B2 | 11/2005 | Knox |
| 7,046,658 B1 | 5/2006 | Kundaje |
| 7,055,174 B1 | 5/2006 | Cope et al. |
| 7,068,772 B1 | 6/2006 | Widger et al. |
| 7,079,526 B1 | 7/2006 | Wipliez et al. |
| 7,120,682 B1 | 10/2006 | Salama |
| 7,212,522 B1 | 5/2007 | Shankar et al. |
| 7,454,200 B2 * | 11/2008 | Cai et al. ................. 455/419 |
| 7,454,510 B2 | 11/2008 | Kleyman et al. |
| 7,950,046 B2 | 5/2011 | Kropivny |
| 8,116,307 B1 | 2/2012 | Thesayi et al. |
| 8,422,507 B2 | 4/2013 | Björsell et al. |
| 8,537,805 B2 | 9/2013 | Björsell et al. |
| 8,542,815 B2 | 9/2013 | Perreault et al. |
| 2002/0051518 A1 | 5/2002 | Bondy et al. |
| 2002/0116464 A1 | 8/2002 | Mak |
| 2002/0122391 A1 | 9/2002 | Shalit |
| 2003/0200311 A1 | 10/2003 | Baum |
| 2003/0219103 A1 | 11/2003 | Rao et al. |
| 2004/0022237 A1 | 2/2004 | Elliot et al. |
| 2004/0157629 A1 | 8/2004 | Kallio et al. |
| 2004/0165709 A1 | 8/2004 | Pence et al. |
| 2004/0181599 A1 | 9/2004 | Kreusch et al. |
| 2004/0202295 A1 | 10/2004 | Shen et al. |
| 2004/0240439 A1 | 12/2004 | Castleberry et al. |
| 2004/0255126 A1 | 12/2004 | Reith |
| 2005/0025043 A1 | 2/2005 | Mussman et al. |
| 2005/0083911 A1 | 4/2005 | Grabelsky et al. |
| 2005/0094651 A1 | 5/2005 | Lutz et al. |
| 2005/0169248 A1 | 8/2005 | Truesdale et al. |
| 2005/0174937 A1 | 8/2005 | Scoggins et al. |
| 2005/0177843 A1 | 8/2005 | Williams |
| 2005/0198499 A1 | 9/2005 | Salapaka et al. |
| 2006/0072547 A1 | 4/2006 | Florkey et al. |
| 2006/0072550 A1 | 4/2006 | Davis et al. |
| 2006/0093135 A1 | 5/2006 | Fiatal et al. |
| 2006/0111116 A1 | 5/2006 | Palmer et al. |
| 2006/0153342 A1 | 7/2006 | Sasaki |
| 2006/0160565 A1 | 7/2006 | Singh et al. |
| 2006/0177035 A1 | 8/2006 | Cope et al. |
| 2006/0209768 A1 | 9/2006 | Yan et al. |
| 2006/0258328 A1 | 11/2006 | Godoy |
| 2006/0264200 A1 | 11/2006 | Laiho et al. |
| 2007/0036143 A1 | 2/2007 | Alt et al. |
| 2007/0112964 A1 | 5/2007 | Guedalia et al. |
| 2007/0127676 A1 | 6/2007 | Khadri |
| 2007/0253418 A1 | 11/2007 | Shiri et al. |
| 2008/0037715 A1 | 2/2008 | Prozeniuk et al. |
| 2008/0056235 A1 | 3/2008 | Albina et al. |
| 2008/0056302 A1 | 3/2008 | Erdal et al. |
| 2008/0063153 A1 | 3/2008 | Krivorot et al. |
| 2009/0028146 A1 | 1/2009 | Kleyman et al. |
| 2009/0135735 A1 | 5/2009 | Zhang et al. |
| 2009/0141883 A1 | 6/2009 | Bastien |
| 2009/0292539 A1 | 11/2009 | Jaroker |
| 2009/0325558 A1 | 12/2009 | Pridmore et al. |
| 2010/0086119 A1 | 4/2010 | De Luca et al. |
| 2010/0128729 A1 | 5/2010 | Yazaki et al. |
| 2012/0099599 A1 | 4/2012 | Keränen et al. |
| 2012/0227101 A1 | 9/2012 | Yuan |
| 2013/0114589 A1 | 5/2013 | Fangman et al. |

FOREIGN PATENT DOCUMENTS

| | | |
|---|---|---|
| EP | 1 389 862 B1 | 11/2004 |
| WO | WO 01/89145 A2 | 11/2001 |
| WO | WO 2007/044454 A2 | 4/2007 |
| WO | WO 2008/052340 A1 | 5/2008 |
| WO | WO 2008/064481 A1 | 6/2008 |
| WO | WO 2008/116296 A1 | 10/2008 |
| WO | WO 2010/012090 A2 | 2/2010 |
| WO | WO 2011/032256 A1 | 3/2011 |

OTHER PUBLICATIONS

ETSI Technical Specification. "Lawful Interception (LI); Handover Interface and Service-Specific Details (SSD) for IP delivery; Part 5:

(56) References Cited

OTHER PUBLICATIONS

Service-specific details for IP Multimedia Services." Apr. 2008, 25 pgs, v.2.3.1, France.

M. Handley et al. "RFC 2543—SIP: Session Initiation Protocol." Mar. 1999.

List of North American Numbering Plan area codes, http://en.wikipedia.org/wiki/List_of_NANP_area_codes; printed Jun. 20, 2012.

Lind AT&T S: "ENUM Call Flows for VoIP Interworking; draft-lind-enum-callflows-03.txt", 20020201, No. 3, Feb. 1, 2002, pp. 1-17, XP015004214, ISSN: 0000-0004.

IETF ENUM WG R STASTNY OEFEG Informational Numbering for VoIP and Other IP Communications: "Numbering for ViOP and other IP Communications, draft-stastny-enum-numbering-voip-00.txt", 20031001, Oct. 1, 2003, pp. 1-43, XP015035676, ISSN: 0000-0004.

F. Baker et al. "RFC 3924—Cisco Architecture for Lawful Intercept in Ip Networks." Oct. 2004.

Cisco. "*Lawful Intercept Requirements Summary*." http://www.faqs.orq/rfcs/rfc3924.html. Nov. 8, 2006.

Sippy Sip B2BUA. "*About Sippy RTPproxy*." http://www.rtpproxy.org. Jul. 15, 2009.

ETSI Technical Specification. "Lawful Interception (LI); Handover Interface and Service-Specific Details (SSD) for IP delivery; Part 5: Service-specific details for IP Multimedia Services." Apr. 2008, 25 pgs., v.2.3.1, France.

M. Handley et al. "RFC 2543—SIP: Session Initiation Protocol." Mar. 1999.

The International Search Report and Written Opinion of the International Searching Authority completed Jun. 6, 2008 for related PCT/CA2008/000545.

The International Search Report and Written Opinion of the International Searching Authority completed Feb. 6, 2008 for corresponding PCT/CA2007/001956.

The International Preliminary Report on Patentability mailed May 14, 2009 for corresponding PCT/CA2007/001956.

The International Search Report and Written Opinion of the International Searching Authority completed Mar. 3, 2008 for related PCT/CA2007/002150.

The International Preliminary Report on Patentability mailed Feb. 13, 2009 for related PCT/CA2007/002150.

The International Preliminary Report on Patentability and Written Opinion of the International Searching Authority mailed Feb. 10, 2011 for related PCT Application No. PCT/CA2009/001062, Feb. 1, 2011.

The Written Opinion and International Search Report completed on Jun. 18, 2010 for related PCT Application No. PCT/CA2009/001317.

The International Search Report and Written Opinion mailed on Mar. 12, 2010 for corresponding PCT Application No. PCT/CA2009/001062.

The International Preliminary Report on Patentability issued on Sep. 29, 2009 for PCT/CA2008/000545.

The International Preliminary Report on Patentability issued on Mar. 20, 2012 for PCT/CA2009/001317.

Townsley, et al.; "RFC 2661—Layer Two Tunneling Protocol 'L2TP'", Aug. 1999.

IP2Location, http://www.ip2location.com/; printed Jun. 20, 2012.

Dots IP Address Validation, "Overview", http://www.serviceobjects.com/products/dots_ipgeo.asp; printed Jun. 21, 2012.

List of North American Numbering Plan area codes, http://en.wikipedia.org/wiki/List_of_NANP_area_codes; printed Jun. 20, 2012.

DOTS Phone Exchange, "Overview", http://www.serviceobjects.com/demos/PhoneExchangeDemo.asp (URL no longer valid, current URL is http://www.serviceobjects.com/products/phone/phone-exchange); printed Jun. 21, 2012.

Rosenberg, et al.; "RFC 3261—SIP: Session Initiation Protocol", Jun. 2002.

Lind AT&T S: "ENUM Call Flows for VoIP Interworking; draft-lind-enum-callflows-03.txt", 20020201, No. 3, Feb. 1, 2002, pp. 1-17, XP015004214, ISSN: 0000-0004.

IETF ENUM WG R STASTNY OEFEG Informational Numbering for VOIP and Other IP Communications: "Numbering for ViOP and other IP Communications, draft-stastny-enumnumbering-voip-00.txt", 20031001, Oct. 1, 2003, pp. 1-43, XP015035676, ISSN: 0000-0004.

Supplementary European Search Report for European Application No. 07816106, dated Jun. 18, 2012.

Supplementary European Search Report for European Application No. 07816106, dated Nov. 2, 2012.

Wikipedia, "International mobile subscriber identity (IMSI)," http://en.wikipedia.org/wiki/IMSI, Jul. 16, 2013.

Wikipedia, "Roaming," http://en.wikipedia.org/wiki/Roaming, Jul. 16, 2013.

Extended European Search Report dated Dec. 20, 2013 for European Application No. 09849358.8 dated Jun. 18, 2012.

* cited by examiner

SIP Invite Message

60 — Caller 2001 1050 8667
62 — Callee 2001 1050 2222
64 — Digest Parameters XXXXXXX
65 — Call ID FF10@ 192.168.0.20
67 — IP Address 192.168.0.20
69 — Caller UDP Port 1

RC Request Message — 150

152 — Caller  2001 1050 8667
154 — Callee  2001 1050 2222
156 — Digest  XXXXXXX
158 — Call ID  FF10@ 192.168.0.20
160 — Type   Subscriber

Dialing Profile for a User ⟵ 253

| | | |
|---|---|---|
| 258 | Username | Assigned on Subscription |
| 260 | Domain | Domain Associated with User |
| 262 | NDD | 1 |
| 264 | IDD | 011 |
| 266 | Country Code | 1 |
| 267 | Local Area Codes | 604;778 |
| 268 | Caller Minimum Local Length | 10 |
| 270 | Caller Maximum Local Length | 10 |
| 273 | Reseller | Retailer |
| 275 | Maximum # of concurrent calls | Assigned on Subscription |
| 277 | Current # of concurrent calls | Assigned on Subscription |

FIG. 9

Dialing Profile for Caller (Vancouver Subscriber) ⟵ 276

| | | |
|---|---|---|
| 258 | Username | 2001 1050 8667 (61 63 70 74, 284) |
| 260 | Domain | sp.yvr.digifonica.com ⟵ 282 (286 288 290) |
| 262 | NDD | 1 |
| 264 | IDD | 011 |
| 266 | Country Code | 1 |
| 267 | Local Area Codes | 604;778 (Vancouver) |
| 268 | Caller Minimum Local Length | 10 |
| 270 | Caller Maximum Local Length | 10 |
| 273 | Reseller | Klondike |
| 275 | Maximum # of concurrent calls | 5 |
| 277 | Current # of concurrent calls | 0 |

FIG. 10

Callee Profile for Calgary Subscriber

| | |
|---:|:---|
| Username | 2001 1050 2222 |
| Domain | sp.yvr.digifonica.com |
| NDD | 1 |
| IDD | 011 |
| Country Code | 1 |
| Local Area Codes | 403 (Calgary) |
| Caller Minimum Local Length | 7 |
| Caller Maximum Local Length | 10 |
| Reseller | Deerfoot |
| Maximum # of concurrent calls | 5 |
| Current # of concurrent calls | 0 |

FIG. 11

Callee Profile for London Subscriber

| | |
|---:|:---|
| Username | 4401 1062 4444 |
| Domain | sp.lhr.digifonica.com |
| NDD | 0 |
| IDD | 00 |
| Country Code | 44 |
| Local Area Codes | 20 (London) |
| Caller Minimum Local Length | 10 |
| Caller Maximum Local Length | 11 |
| Reseller | Marble Arch |
| Maximum # of concurrent calls | 5 |
| Current # of concurrent calls | 0 |

FIG. 12

DID Bank Table Record Format ←—278

- 281 —~— Username — System subscriber
- 272 —~— User Domain — Host name of supernode
- 274 —~— DID — E164#

FIG. 13

DID Bank Table Record for Calgary Subscriber ←—300
                                      61

- 281 —~— Username — 2001 1050 2222
- 272 —~— User Domain — Sp.yvr.digifonica.com
- 274 —~— DID — 1 604 867 5309

Routing Message Format ␣␣␣␣ /―352

| | | |
|---|---|---|
| 354 — | Supplier Prefix (optional) | Code identifying supplier traffic |
| 356 — | Delimiter (optional) | Symbol separating fields |
| 358 — | Callee | PSTN compatible number or Digifonica number |
| 360 — | Route | Domain name or IP address |
| 362 — | Time to Live(TTL) | In seconds |
| 364 — | Other | TBD |

FIG. 15

Example of Routing Message – Different Node /―366

440110624444@sp.lhr.digifonica.com;ttl=9999
⎵⎵⎵⎵⎵⎵⎵⎵⎵  ⎵⎵⎵⎵⎵⎵⎵⎵⎵⎵⎵⎵⎵⎵⎵⎵  ⎵⎵⎵⎵⎵⎵
      359                  361              363

FIG. 16

Prefix to Supernode Table Record Format /―370

| | | |
|---|---|---|
| 372 — | Prefix | First n digits of callee identifier |
| 374 — | Supernode Address | IP address or fully qualified domain name |

FIG. 17

Prefix to Supernode Table Record for Calgary Subscriber

| | |
|---|---|
| Prefix | 20 |
| Supernode Address | sp.yvr.digifonica.com |

FIG. 18

Master List Record Format

| | | |
|---|---|---|
| 500 — | ml_id | Alphanumeric |
| 502 — | Dialing code | Number Sequence |
| 504 — | Country code | The country code is the national prefix to be used when dialing TO a particular country FROM another country. |
| 506 — | Nat Sign #(Area Code) | Number Sequence |
| 508 — | Min Length | Numeric |
| 510 — | Max Length | Numeric |
| 512 — | NDD | The NDD prefix is the access code used to make a call WITHIN that country from one city to another (when calling another city in the same vicinity, this may not be necessary). |
| 514 — | IDD | The IDD prefix is the international prefix needed to dial a call FROM the country listed TO another country. |
| 516 — | Buffer rate | Safe change rate above the highest rate charged by suppliers |

FIG. 19

Example: Master List Record with Populated Fields

| | |
|---|---|
| ml_id | 1019 |
| Dialing code | 1604 |
| Country code | 1 |
| Nat Sign #(Area Code) | 604 |
| Min Length | 7 |
| Max Length | 7 |
| NDD | 1 |
| IDD | 011 |
| Buffer rate | $0.009/min |

FIG. 20

Suppliers List Record Format

| | | |
|---|---|---|
| 540 ~ | Sup_id | Name code |
| 542 ~ | MI_id | Numeric code |
| 544 ~ | Prefix (optional) | String identifying supplier's traffic # |
| 546 ~ | Specific Route | IP address |
| 548 ~ | NDD/IDD rewrite | |
| 550 ~ | Rate | Cost per second to Digifonica to use this route |
| 551 ~ | Timeout | Maximum time to wait for a response when requesting this gateway |

FIG. 21

Telus Supplier Record

| | |
|---|---|
| Sup_id | 2010 (Telus) |
| MI_id | 1019 |
| Prefix (optional) | 4973# |
| Specific Route | 72.64.39.58 |
| NDD/IDD rewrite | 011 |
| Rate | $0.02/min |
| Timeout | 20 |

FIG. 22

Shaw Supplier Record

| | |
|---|---|
| Sup_id | 2011 (Shaw) |
| MI_id | 1019 |
| Prefix (optional) | 4974# |
| Specific Route | 73.65.40.59 |
| NDD/IDD rewrite | 011 |
| Rate | $0.025/min |
| Timeout | 30 |

FIG. 23

Sprint Supplier Record

| | |
|---|---|
| Sup_id | 2012 (Sprint) |
| MI_id | 1019 |
| Prefix (optional) | 4975# |
| Specific Route | 74.66.41.60 |
| NDD/IDD rewrite | 011 |
| Rate | $0.03/min |
| Timeout | 40 |

FIG. 24

Routing Message Buffer for Gateway Call

4973#0116048675309@72.64.39.58;ttl=3600;to=20 —— 570
4974#0116048675309@73.65.40.59;ttl=3600;to=30 —— 572
4975#0116048675309@74.66.41.60;ttl=3600;to=40 —— 574

FIG. 25

Call Block Table Record Format

| | | |
|---|---|---|
| 604 —— | Username | Digifonica # |
| 606 —— | Block Pattern | PSTN compatible or Digifonica # |

FIG. 26

Call Block Table Record for Calgary Callee

| | | |
|---|---|---|
| 604 —— | Username of Callee | 2001 1050 2222 |
| 606 —— | Block Pattern | 2001 1050 8664 |

FIG. 27

Call Forwarding Table Record Format for Callee

| | | |
|---|---|---|
| 614 —— | Username of Callee | Digifonica # |
| 616 —— | Destination Number | Digifonica # |
| 618 —— | Sequence Number | Integer indicating order to try this |

FIG. 28

Call Forwarding Table Record for Calgary Callee

| | | |
|---|---|---|
| 614 —— | Username of Callee | 2001 1050 2222 |
| 616 —— | Destination Number | 2001 1055 2223 |
| 618 —— | Sequence Number | 1 |

FIG. 29

Voicemail Table Record Format

- 624 — Username of Callee    Digifonica #
- 626 — Vm Server    domain name
- 628 — Seconds to Voicemail    time to wait before engaging voicemail
- 630 — Enabled    yes/no

FIG. 30

Voicemail Table Record for Calgary Callee

| | |
|---|---|
| Username of Callee | 2001 1050 2222 |
| Vm Server | vm.yvr.digifonica.com |
| Seconds to Voicemail | 20 |
| Enabled | 1 |

FIG. 31

Routing Message Buffer – Same Node

- 650 — 200110502222@sp.yvr.digifonica.com;ttl=3600
- 652 — 200110552223@sp.yvr.digifonica.com;ttl=3600
- 654 — vm.yvr.digifonica.com;20;ttl=60
- 656 — sp.yvr.digifonica.com

FIG. 32

Subscriber Bundle Table Record  /706

- 708 — Username — Subscriber username
- 710 — Services — Codes identifying service features (e.g. Free local calling; call blocking, voicemail)

FIG. 34

Subscriber Bundle Record for Vancouver Caller

- 708 — Username — 2001 1050 8667
- 710 — Services — 10; 14; 16

FIG. 35

Bundle Override Table Record  /714

- 716 — ML_Id — Master list ID code
- 718 — Override type — Fixed; percent; cents
- 720 — Override value — real number representing value of override type
- 722 — Inc1 — first level of charging (minimum # of seconds) charge
- 724 — Inc2 — second level of charging

FIG. 36

Bundle Override Record for Located ML_ID  /726

- 716 — ML_Id — 1019
- 718 — Override type — percent
- 720 — Override value — 10.0
- 722 — Inc1 — 30 seconds
- 724 — Inc2 — 6 seconds

FIG. 37

Subscriber Account Table Record /736

- 738 — Username — Subscriber username
- 740 — Funds balance — real number representing $ value of credit
- 742 — Free time balance — integer representing # of free seconds

FIG. 38

Subscriber Account Record for Vancouver Caller /744

- 738 — Username — 2001 1050 8667
- 740 — Funds balance — $10.00
- 742 — Free time balance — 100

System Operator Special Rates Table Record

| | | |
|---|---|---|
| 786 — | Reseller | retailer id |
| 788 — | ML_Id | master list id |
| 790 — | Markup Table | fixed; percent; cents |
| 792 — | Markup Value | real number representing value of markup type |
| 794 — | Inc1 | first level of charging (minimum # of seconds) charge |
| 796 — | Inc2 | second level of charging |

System Operator Special Rates Table Record for Klondike

| | | |
|---|---|---|
| 786 — | Reseller | Klondike |
| 788 — | ML_Id | 1019 |
| 790 — | Markup Table | cents |
| 792 — | Markup Value | $0.001 |
| 794 — | Inc1 | 30 |
| 796 — | Inc2 | 6 |

FIG. 43

System Operator Markup Table Record /804

| | | |
|---|---|---|
| 806 — | Reseller | reseller id code |
| 808 — | Markup Table | fixed; percent; cents |
| 810 — | Markup Value | real number representing value of markup type |
| 812 — | Inc1 | first level of charging (minimum # of seconds) charge |
| 814 — | Inc2 | second level of charging |

FIG. 44

System Operator Markup Table Record for the Reseller Klondike

| | | |
|---|---|---|
| 806 — | Reseller | Klondike |
| 808 — | Markup Table | cents |
| 810 — | Markup Value | $0.01 |
| 812 — | Inc1 | 30 |
| 814 — | Inc2 | 6 |

FIG. 45

System Operator Markup Table Record

| | | |
|---|---|---|
| 806 — | Reseller | all |
| 808 — | Markup Table | percent |
| 810 — | Markup Value | 1.0 |
| 812 — | Inc1 | 30 |
| 814 — | Inc2 | 6 |

FIG. 46

Reseller Special Destinations Table Record  /832

- 834 — Reseller — reseller id code
- 836 — ML_Id — Master List ID code
- 838 — Markup Table — fixed; percent; cents
- 840 — Markup Value — real number representing value of markup type
- 842 — Inc1 — first level of charging (minimum # of seconds) charge
- 844 — Inc2 — second level of charging

FIG. 47

Reseller Special Destinations Table Record for the Reseller Klondike  /846

- 834 — Reseller — Klondike
- 836 — ML_Id — 1019
- 838 — Markup Table — percent
- 840 — Markup Value — 5%
- 842 — Inc1 — 30
- 844 — Inc2 — 6

FIG. 48

Reseller Global Markup Table Record  /848

- 850 — Reseller — reseller id code
- 852 — Markup Table — fixed; percent; cents
- 854 — Markup Value — real number representing value of markup type
- 856 — Inc1 — first level of charging (minimum # of seconds) charge
- 858 — Inc2 — second level of charging

FIG. 49

Reseller Global Markup Table Record for the Reseller Klondike  /860

- 850 — Reseller — Klondike
- 852 — Markup Table — percent
- 854 — Markup Value — 10%
- 856 — Inc1 — 30
- 858 — Inc2 — 6

FIG. 50

SIP Bye Message

| | | |
|---|---|---|
| 902 — | Caller | Username |
| 904 — | Callee | PSTN compatible # or Username |
| 906 — | Call ID | unique call identifier (hexadecimal string@IP)) |

SIP Bye Message

| | | |
|---|---|---|
| 902 — | Caller | 2001 1050 8667 |
| 904 — | Callee | 2001 1050 2222 |
| 906 — | Call ID | FA10@192.168.0.20 |

RC Call Stop Message /1000

| | | |
|---|---|---|
| 1002 | Caller | Username |
| 1004 | Callee | PSTN compatible # or Username |
| 1006 | Call ID | unique call identifier (hexadecimal string@IP) |
| 1008 | Acct Start Time | start time of call |
| 1010 | Acct Stop Time | time the call ended |
| 1012 | Acct Session Time | start time-stop time (in seconds) |
| 1014 | Route | IP address for the communications link that was established |

FIG. 54

RC Call Stop Message for Calgary Callee /1020

| | | |
|---|---|---|
| 1002 | Caller | 2001 1050 8667 |
| 1004 | Callee | 2001 1050 2222 |
| 1006 | Call ID | FA10@192.168.0.20 |
| 1008 | Acct Start Time | 2006-12-30 12:12:12 |
| 1010 | Acct Stop Time | 2006-12-30 12:12:14 |
| 1012 | Acct Session Time | 2 |
| 1014 | Route | 72.64.39.58 |

FIG. 55

Reseller Accounts Table Record / 982

984 — Reseller ID     reseller id code
986 — Reseller balance     accumulated balance of charges

FIG. 57

Reseller Accounts Table Record for Klondike / 988

984 — Reseller ID     Klondike
986 — Reseller balance     $100.02

FIG. 58

System Operator Accounts Table Record / 994

996 — System Operator balance     accumulated balance of charges

FIG. 59

System Operator Accounts Record for this System Operator

996 — System Operator balance     $1000.02

FIG. 60

ALLOCATING CHARGES FOR COMMUNICATIONS SERVICES

CROSS REFERENCE TO RELATED APPLICATIONS

This application is a continuation of U.S. application Ser. No. 12/513,147, filed Mar. 1, 2010, which is a national phase entry of PCT/CA2007/001956, filed Nov. 1, 2007, which claims priority to U.S. Provisional Application No. 60/856,212, filed Nov. 2, 2006, all of which are incorporated in their entirety.

BACKGROUND OF THE INVENTION

1. Field of Invention

This invention relates to voice over IP communications and methods and apparatus for routing and billing.

2. Description of Related Art

Internet protocol (IP) telephones are typically personal computer (PC) based telephones connected within an IP network, such as the public Internet or a private network of a large organization. These IP telephones have installed "voice-over-IP" (VoIP) software enabling them to make and receive voice calls and send and receive information in data and video formats.

IP telephony switches installed within the IP network enable voice calls to be made within or between IP networks, and between an IP network and a switched circuit network (SCN), such as the public switched telephone network (PSTN). If the IP switch supports the Signaling System 7 (SS7) protocol, the IP telephone can also access PSTN databases.

The PSTN network typically includes complex network nodes that contain all information about a local calling service area including user authentication and call routing. The PSTN network typically aggregates all information and traffic into a single location or node, processes it locally and then passes it on to other network nodes, as necessary, by maintaining route tables at the node. PSTN nodes are redundant by design and thus provide reliable service, but if a node should fail due to an earthquake or other natural disaster, significant, if not complete service outages can occur, with no other nodes being able to take up the load.

Existing VoIP systems do not allow for high availability and resiliency in delivering Voice Over IP based Session Initiation Protocol (SIP) Protocol service over a geographically dispersed area such as a city, region or continent. Most resiliency originates from the provision of IP based telephone services to one location or a small number of locations such as a single office or network of branch offices.

SUMMARY OF THE INVENTION

In accordance with one aspect of the invention, there is provided a process for operating a call routing controller to facilitate communication between callers and callees in a system comprising a plurality of nodes with which callers and callees are associated. The process involves, in response to initiation of a call by a calling subscriber, receiving a caller identifier and a callee identifier. The process also involves using call classification criteria associated with the caller identifier to classify the call as a public network call or a private network call. The process further involves producing a routing message identifying an address, on the private network, associated with the callee when the call is classified as a private network call. The process also involves producing a routing message identifying a gateway to the public network when the call is classified as a public network call.

The process may involve receiving a request to establish a call, from a call controller in communication with a caller identified by the callee identifier.

Using the call classification criteria may involve searching a database to locate a record identifying calling attributes associated with a caller identified by the caller identifier.

Locating a record may involve locating a caller dialing profile comprising a username associated with the caller, a domain associated with the caller, and at least one calling attribute.

Using the call classification criteria may involve comparing calling attributes associated with the caller dialing profile with aspects of the callee identifier.

Comparing may involve determining whether the callee identifier includes a portion that matches an IDD associated with the caller dialing profile.

Comparing may involve determining whether the callee identifier includes a portion that matches an NDD associated with the caller dialing profile.

Comparing may involve determining whether the callee identifier includes a portion that matches an area code associated with the caller dialing profile.

Comparing may involve determining whether the callee identifier has a length within a range specified in the caller dialing profile.

The process may involve formatting the callee identifier into a pre-defined digit format to produce a re-formatted callee identifier.

Formatting may involve removing an international dialing digit from the callee identifier, when the callee identifier begins with a digit matching an international dialing digit specified by the caller dialing profile associated with the caller.

Formatting may involve removing a national dialing digit from the callee identifier and prepending a caller country code to the callee identifier when the callee identifier begins with a national dialing digit.

Formatting may involve prepending a caller country code to the callee identifier when the callee identifier begins with digits identifying an area code specified by the caller dialing profile.

Formatting may involve prepending a caller country code and an area code to the callee identifier when the callee identifier has a length that matches a caller dialing number format specified by the caller dialing profile and only one area code is specified as being associated with the caller in the caller dialing profile.

The process may involve classifying the call as a private network call when the re-formatted callee identifier identifies a subscriber to the private network.

The process may involve determining whether the callee identifier complies with a pre-defined username format and if so, classifying the call as a private network call.

The process may involve causing a database of records to be searched to locate a direct in dial (DID) bank table record associating a public telephone number with the reformatted callee identifier and if the DID bank table record is found, classifying the call as a private network call and if a DID bank table record is not found, classifying the call as a public network call.

Producing the routing message identifying a node on the private network may involve setting a callee identifier in response to a username associated with the DID bank table record.

Producing the routing message may involve determining whether a node associated with the reformatted callee identifier is the same as a node associated the caller identifier.

Determining whether a node associated with the reformatted callee identifier is the same as a node associated the caller identifier may involve determining whether a prefix of the re-formatted callee identifier matches a corresponding prefix of a username associated with the caller dialing profile.

When the node associated with the caller is not the same as the node associated with the callee, the process involves producing a routing message including the caller identifier, the reformatted callee identifier and an identification of a private network node associated with the callee and communicating the routing message to a call controller.

When the node associated with the caller is the same as the node associated with the callee, the process involves determining whether to perform at least one of the following: forward the call to another party, block the call and direct the caller to a voicemail server associated with the callee.

Producing the routing message may involve producing a routing message having an identification of at least one of the callee identifier, an identification of a party to whom the call should be forwarded and an identification of a voicemail server associated with the callee.

Producing a routing message identifying a gateway to the public network may involve searching a database of route records associating route identifiers with dialing codes to find a route record having a dialing code having a number pattern matching at least a portion of the reformatted callee identifier.

The process may involve communicating the routing message to a call controller.

The process may involve searching a database of supplier records associating supplier identifiers with the route identifiers to locate at least one supplier record associated with the route identifier associated with the route record having a dialing code having a number pattern matching at least a portion of the reformatted callee identifier.

The process may involve loading a routing message buffer with the reformatted callee identifier and an identification of specific routes associated respective ones of the supplier records associated with the route record and loading the routing message buffer with a time value and a timeout value.

The process may involve communicating a routing message involving the contents of the routing message buffer to a call controller.

The process may involve causing the dialing profile to include a maximum concurrent call value and a concurrent call count value and causing the concurrent call count value to be incremented when the user associated with the dialing profile initiates a call and causing the concurrent call count value to be decremented when a call with the user associated with the dialing profile is ended.

In accordance with another aspect of the invention, there is provided a call routing apparatus for facilitating communications between callers and callees in a system comprising a plurality of nodes with which callers and callees are associated. The apparatus includes receiving provisions for receiving a caller identifier and a callee identifier, in response to initiation of a call by a calling subscriber. The apparatus also includes classifying provisions for classifying the call as a private network cal or a public network call according to call classification criteria associated with the caller identifier. The apparatus further includes provisions for producing a routing message identifying an address, on the private network, associated with the callee when the call is classified as a private network call. The apparatus also includes provisions for producing a routing message identifying a gateway to the public network when the call is classified as a public network call.

The receiving provisions may be operably configured to receive a request to establish a call, from a call controller in communication with a caller identified by the callee identifier.

The apparatus may further include searching provisions for searching a database including records associating calling attributes with subscribers to the private network to locate a record identifying calling attributes associated with a caller identified by the caller identifier.

The records may include dialing profiles each including a username associated with the subscriber, an identification of a domain associated with the subscriber, and an identification of at least one calling attribute associated with the subscriber.

The call classification provisions may be operably configured to compare calling attributes associated with the caller dialing profile with aspects of the callee identifier.

The calling attributes may include an international dialing digit and call classification provisions may be operably configured to determine whether the callee identifier includes a portion that matches an IDD associated with the caller dialing profile.

The calling attributes may include an national dialing digit and the call classification provisions may be operably configured to determine whether the callee identifier includes a portion that matches an NDD associated with the caller dialing profile.

The calling attributes may include an area code and the call classification provisions may be operably configured to determine whether the callee identifier includes a portion that matches an area code associated with the caller dialing profile.

The calling attribute may include a number length range and the call classification provisions may be operably configured to determine whether the callee identifier has a length within a number length range specified in the caller dialing profile.

The apparatus may further include formatting provisions for formatting the callee identifier into a pre-defined digit format to produce a re-formatted callee identifier.

The formatting provisions may be operably configured to remove an international dialing digit from the callee identifier, when the callee identifier begins with a digit matching an international dialing digit specified by the caller dialing profile associated with the caller.

The formatting provisions may be operably configured to remove a national dialing digit from the callee identifier and prepend a caller country code to the callee identifier when the callee identifier begins with a national dialing digit.

The formatting provisions may be operably configured to prepend a caller country code to the callee identifier when the callee identifier begins with digits identifying an area code specified by the caller dialing profile.

The formatting provisions may be operably configured to prepend a caller country code and area code to the callee identifier when the callee identifier has a length that matches a caller dialing number format specified by the caller dialing profile and only one area code is specified as being associated with the caller in the caller dialing profile.

The classifying provisions may be operably configured to classify the call as a private network call when the re-formatted callee identifier identifies a subscriber to the private network.

The classifying provisions may be operably configured to classify the call as a private network call when the callee identifier complies with a pre-defined username format.

The apparatus may further include searching provisions for searching a database of records to locate a direct in dial (DID) bank table record associating a public telephone number with the reformatted callee identifier and the classifying provisions may be operably configured to classify the call as a private network call when the DID bank table record is found and to classify the call as a public network call when a DID bank table record is not found The private network routing message producing provisions may be operably configured to produce a routing message having a callee identifier set according to a username associated with the DID bank table record.

The private network routing message producing provisions may be operably configured to determine whether a node associated with the reformatted callee identifier is the same as a node associated the caller identifier.

The private network routing provisions may include provisions for determining whether a prefix of the re-formatted callee identifier matches a corresponding prefix of a username associated with the caller dialing profile.

The private network routing message producing provisions may be operably configured to produce a routing message including the caller identifier, the reformatted callee identifier and an identification of a private network node associated with the callee and to communicate the routing message to a call controller.

The private network routing message producing provisions may be operably configured to perform at least one of the following forward the call to another party, block the call and direct the caller to a voicemail server associated with the callee, when the node associated with the caller is the same as the node associated with the callee.

The provisions for producing the private network routing message may be operably configured to produce a routing message having an identification of at least one of the callee identifier, an identification of a party to whom the call should be forwarded and an identification of a voicemail server associated with the callee.

The apparatus further includes provisions for communicating the routing message to a call controller.

The provisions for producing a public network routing message identifying a gateway to the public network may include provisions for searching a database of route records associating route identifiers with dialing codes to find a route record having a dialing code having a number pattern matching at least a portion of the reformatted callee identifier.

The apparatus further includes provisions for searching a database of supplier records associating supplier identifiers with the route identifiers to locate at least one supplier record associated with the route identifier associated with the route record having a dialing code having a number pattern matching at least a portion of the reformatted callee identifier.

The apparatus further includes a routing message buffer and provisions for loading the routing message buffer with the reformatted callee identifier and an identification of specific routes associated respective ones of the supplier records associated with the route record and loading the routing message buffer with a time value and a timeout value.

The apparatus further includes provisions for communicating a routing message including the contents of the routing message buffer to a call controller.

The apparatus further includes means for causing the dialing profile to include a maximum concurrent call value and a concurrent call count value and for causing the concurrent call count value to be incremented when the user associated with the dialing profile initiates a call and for causing the concurrent call count value to be decremented when a call with the user associated with the dialing profile is ended.

In accordance with another aspect of the invention, there is provided a data structure for access by an apparatus for producing a routing message for use by a call routing controller in a communications system. The data structure includes dialing profile records comprising fields for associating with respective subscribers to the system, a subscriber user name, direct-in-dial records comprising fields for associating with respective subscriber usernames, a user domain and a direct-in-dial number, prefix to node records comprising fields for associating with at least a portion of the respective subscriber usernames, a node address of a node in the system, whereby a subscriber name can be used to find a user domain, at least a portion of the a subscriber name can be used to find a node with which the subscriber identified by the subscriber name is associated, and a user domain and subscriber name can be located in response to a direct-in-dial number.

In accordance with another aspect of the invention, there is provided a data structure for access by an apparatus for producing a routing message for use by a call routing controller in a communications system. The data structure includes master list records comprising fields for associating a dialing code with respective master list identifiers and supplier list records linked to master list records by the master list identifiers, the supplier list records comprising fields for associating with a communications services supplier, a supplier id, a master list id, a route identifier and a billing rate code, whereby communications services suppliers are associated with dialing codes, such that dialing codes can be used to locate suppliers capable of providing a communications link associated with a given dialing code.

In accordance with another aspect of the invention, there is provided a method for determining a time to permit a communication session to be conducted. The method involves calculating a cost per unit time, calculating a first time value as a sum of a free time attributed to a participant in the communication session and the quotient of a funds balance held by the participant to the cost per unit time value and producing a second time value in response to the first time value and a billing pattern associated with the participant, the billing pattern including first and second billing intervals and the second time value being the time to permit a communication session to be conducted.

Calculating the first time value may involve retrieving a record associated with the participant and obtaining from the record at least one of the free time and the funds balance.

Producing the second time value may involve producing a remainder value representing a portion of the second billing interval remaining after dividing the second billing interval into a difference between the first time value and the first billing interval.

Producing the second time value may involve setting a difference between the first time value and the remainder as the second time value.

The method may further involve setting the second time value to zero when the remainder is greater than zero and the first time value is less than the free time associated with the participant.

Calculating the cost per unit time may involve locating a record in a database, the record comprising a markup type indicator, a markup value and a billing pattern and setting a reseller rate equal to the sum of the markup value and the buffer rate.

Locating the record in a database may involve locating at least one of a record associated with a reseller and a route associated with the reseller, a record associated with the reseller and a default reseller markup record.

Calculating the cost per unit time value further may involve locating at least one of an override record specifying a route cost per unit time amount associated with a route associated with the communication session, a reseller record associated with a reseller of the communications session, the reseller record specifying a reseller cost per unit time associated with the reseller for the communication session, a default operator markup record specifying a default cost per unit time.

The method may further involve setting as the cost per unit time the sum of the reseller rate and at least one of the route cost per unit time, the reseller cost per unit time and the default cost per unit time.

The method may further involve receiving a communication session time representing a duration of the communication session and incrementing a reseller balance by the product of the reseller rate and the communication session time.

The method may further involve receiving a communication session time representing a duration of the communication session and incrementing a system operator balance by a product of the buffer rate and the communication session time.

In accordance with another aspect of the invention, there is provided an apparatus for determining a time to permit a communication session to be conducted. The apparatus includes a processor circuit, a computer readable medium coupled to the processor circuit and encoded with instructions for directing the processor circuit to calculate a cost per unit time for the communication session, calculate a first time value as a sum of a free time attributed to a participant in the communication session and the quotient of a funds balance held by the participant to the cost per unit time value and produce a second time value in response to the first time value and a billing pattern associated with the participant, the billing pattern including first and second billing intervals and the second time value being the time to permit a communication session to be conducted.

The instructions may include instructions for directing the processor circuit to retrieve a record associated with the participant and obtain from the record at least one of the free time and the funds balance.

The instructions may include instructions for directing the processor circuit to produce the second time value by producing a remainder value representing a portion of the second billing interval remaining after dividing the second billing interval into a difference between the first time value and the first billing interval.

The instructions may include instructions for directing the processor circuit to produce the second time value comprises setting a difference between the first time value and the remainder as the second time value.

The instructions may include instructions for directing the processor circuit to set the second time value to zero when the remainder is greater than zero and the first time value is less than the free time associated with the participant.

The instructions for directing the processor circuit to calculate the cost per unit time may include instructions for directing the processor circuit to locate a record in a database, the record comprising a markup type indicator, a markup value and a billing pattern and set a reseller rate equal to the sum of the markup value and the buffer rate.

The instructions for directing the processor circuit to locate the record in a database may include instructions for directing the processor circuit to locate at least one of a record associated with a reseller and a route associated with the reseller, a record associated with the reseller, and a default reseller markup record. The instructions for directing the processor circuit to calculate the cost per unit time value may further include instructions for directing the processor circuit to locate at least one of an override record specifying a route cost per unit time amount associated with a route associated with the communication session, a reseller record associated with a reseller of the communications session, the reseller record specifying a reseller cost per unit time associated with the reseller for the communication session, a default operator markup record specifying a default cost per unit time.

The instructions may include instructions for directing the processor circuit to set as the cost per unit time the sum of the reseller rate and at least one of the route cost per unit time, the reseller cost per unit time and the default cost per unit time.

The instructions may include instructions for directing the processor circuit to receive a communication session time representing a duration of the communication session and increment a reseller balance by the product of the reseller rate and the communication session time.

The instructions may include instructions for directing the processor circuit to receive a communication session time representing a duration of the communication session and increment a system operator balance by a product of the buffer rate and the communication session time.

In accordance with another aspect of the invention, there is provided a process for attributing charges for communications services. The process involves determining a first chargeable time in response to a communication session time and a pre-defined billing pattern, determining a user cost value in response to the first chargeable time and a free time value associated with a user of the communications services, changing an account balance associated with the user in response to a user cost per unit time. The process may further involve changing an account balance associated with a reseller of the communications services in response to a reseller cost per unit time and the communication session time and changing an account balance associated with an operator of the communications services in response to an operator cost per unit time and the communication session time.

Determining the first chargeable time may involve locating at least one of an override record specifying a route cost per unit time and billing pattern associated with a route associated with the communication session, a reseller record associated with a reseller of the communications session, the reseller record specifying a reseller cost per unit time and billing pattern associated with the reseller for the communication session and a default record specifying a default cost per unit time and billing pattern and setting as the pre-defined billing pattern the billing pattern of the record located. The billing pattern of the record located may involve a first billing interval and a second billing interval.

Determining the first chargeable time may involve setting the first chargeable time equal to the first billing interval when the communication session time is less than or equal to the first billing interval.

Determining the first chargeable time may involve producing a remainder value representing a portion of the second billing interval remaining after dividing the second billing interval into a difference between communication session time and the first interval when the communication session time is greater than the communication session time and setting the first chargeable time to a difference between the communication session time and the remainder when the remainder is greater than zero and setting the first chargeable time to the communication session time when the remainder is not greater than zero.

The process may further involve determining a second chargeable time in response to the first chargeable time and the free time value associated with the user of the communications services when the first chargeable time is greater than or equal to the free time value associated with the user of the communications services.

Determining the second chargeable time may involve setting the second chargeable time to a difference between the first chargeable time.

The process may further involve resetting the free time value associated with the user to zero when the first chargeable time is greater than or equal to the free time value associated with the user of the communications services.

Changing an account balance associated with the user may involve calculating a user cost value in response to the second chargeable time and the user cost per unit time.

The process may further involve changing a user free cost balance in response to the user cost value.

The process may further involve setting the user cost to zero when the first chargeable time is less than the free time value associated with the user.

The process may further involve changing a user free time balance in response to the first chargeable time.

In accordance with another aspect of the invention, there is provided an apparatus for attributing charges for communications services. The apparatus includes a processor circuit, a computer readable medium in communication with the processor circuit and encoded with instructions for directing the processor circuit to determine a first chargeable time in response to a communication session time and a pre-defined billing pattern, determine a user cost value in response to the first chargeable time and a free time value associated with a user of the communications services, change an account balance associated with the user in response to a user cost per unit time.

The instructions may further include instructions for changing an account balance associated with a reseller of the communications services in response to a reseller cost per unit time and the communication session time and changing an account balance associated with an operator of the communications services in response to an operator cost per unit time and the communication session time.

The instructions for directing the processor circuit to determine the first chargeable time may further include instructions for causing the processor circuit to communicate with a database to locate at least one of an override record specifying a route cost per unit time and billing pattern associated with a route associated with the communication session, a reseller record associated with a reseller of the communications session, the reseller record specifying a reseller cost per unit time and billing pattern associated with the reseller for the communication session and a default record specifying a default cost per unit time and billing pattern and instructions for setting as the pre-defined billing pattern the billing pattern of the record located. The billing pattern of the record located may include a first billing interval and a second billing interval.

The instructions for causing the processor circuit to determine the first chargeable time may include instructions for directing the processor circuit to set the first chargeable time equal to the first billing interval when the communication session time is less than or equal to the first billing interval.

The instructions for causing the processor circuit to determine the first chargeable time may include instructions for producing a remainder value representing a portion of the second billing interval remaining after dividing the second billing interval into a difference between communication session time and the first interval when the communication session time is greater than the communication session time and instructions for causing the processor circuit to set the first chargeable time to a difference between the communication session time and the remainder when the remainder is greater than zero and instructions for causing the processor circuit to set the first chargeable time to the communication session time when the remainder is not greater than zero.

The instructions may further include instructions for causing the processor circuit to determine a second chargeable time in response to the first chargeable time and the free time value associated with the user of the communications services when the first chargeable time is greater than or equal to the free time value associated with the user of the communications services.

The instructions for causing the processor circuit to determine the second chargeable time may include instructions for causing the processor circuit to set the second chargeable time to a difference between the first chargeable time.

The instructions may further include instructions for causing the processor circuit to reset the free time value associated with the user to zero when the first chargeable time is greater than or equal to the free time value associated with the user of the communications services.

The instructions for causing the processor circuit to change an account balance associated with the user may include instructions for causing the processor circuit to calculate a user cost value in response to the second chargeable time and the user cost per unit time.

The instructions may further include instructions for causing the processor circuit to change a user free cost balance in response to the user cost value.

The instructions may further include instructions for causing the processor circuit to set the user cost to zero when the first chargeable time is less than the free time value associated with the user.

The instructions may further include instructions for causing the processor circuit to change a user free time balance in response to the first chargeable time.

In accordance with another aspect of the invention, there is provided a computer readable medium encoded with codes for directing a processor circuit to execute one or more of the methods described above and/or variants thereof Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 9 is a tabular representation of a dialing profile stored in a database accessible by the RC shown in FIG. 1;

FIG. 10 is a tabular representation of a dialing profile for a caller using the caller telephone shown in FIG. 1;

FIG. 11 is a tabular representation of a callee profile for a callee located in Calgary;

FIG. 12 is a tabular representation of a callee profile for a callee located in London;

FIG. 13 is a tabular representation of a Direct-in-Dial (DID) bank table record stored in the database shown in FIG. 1;

FIG. 14 is a tabular representation of an exemplary DID bank table record for the Calgary callee referenced in FIG. 11;

FIG. 15 is a tabular representation of a routing message transmitted from the RC to the call controller shown in FIG. 1;

FIG. 16 is a schematic representation of a routing message buffer holding a routing message for routing a call to the Calgary callee referenced in FIG. 11;

FIG. 17 is a tabular representation of a prefix to supernode table record stored in the database shown in FIG. 1;

FIG. 18 is a tabular representation of a prefix to supernode table record that would be used for the Calgary callee referenced in FIG. 11;

FIG. 19 is a tabular representation of a master list record stored in a master list table in the database shown in FIG. 1;

FIG. 20 is a tabular representation of a populated master list record;

FIG. 21 is a tabular representation of a suppliers list record stored in the database shown in FIG. 1;

FIG. 22 is a tabular representation of a specific supplier list record for a first supplier;

FIG. 23 is a tabular representation of a specific supplier list record for a second supplier;

FIG. 24 is a tabular representation of a specific supplier list record for a third supplier;

FIG. 25 is a schematic representation of a routing message, held in a routing message buffer, identifying to the controller a plurality of possible suppliers that may carry the call;

FIG. 26 is a tabular representation of a call block table record;

FIG. 27 is a tabular representation of a call block table record for the Calgary callee;

FIG. 28 is a tabular representation of a call forwarding table record;

FIG. 29 is a tabular representation of a call forwarding table record specific for the Calgary callee;

FIG. 30 is a tabular representation of a voicemail table record specifying voicemail parameters to enable the caller to leave a voicemail message for the callee;

FIG. 31 is a tabular representation of a voicemail table record specific to the Calgary callee;

FIG. 32 is a schematic representation of an exemplary routing message, held in a routing message buffer, indicating call forwarding numbers and a voicemail server identifier;

FIG. 34 is a tabular representation of a subscriber bundle table record;

FIG. 35 is a tabular representation of a subscriber bundle record for the Vancouver caller;

FIG. 36 is a tabular representation of a bundle override table record;

FIG. 37 is a tabular representation of bundle override record for a located master list ID;

FIG. 38 is a tabular representation of a subscriber account table record;

FIG. 39 is a tabular representation of a subscriber account record for the Vancouver caller;

FIG. 42 is a tabular representation of a system operator special rates table record;

FIG. 43 is a tabular representation of a system operator special rates table record for a reseller named Klondike;

FIG. 44 is a tabular representation of a system operator mark-up table record;

FIG. 45 is a tabular representation of a system operator mark-up table record for the reseller Klondike;

FIG. 46 is a tabular representation of a default system operator mark-up table record;

FIG. 47 is a tabular representation of a reseller special destinations table record;

FIG. 48 is a tabular representation of a reseller special destinations table record for the reseller Klondike;

FIG. 49 is a tabular representation of a reseller global mark-up table record;

FIG. 50 is a tabular representation of a reseller global mark-up table record for the reseller Klondike;

FIG. 51 is a tabular representation of a SIP bye message transmitted from either of the telephones shown in FIG. 1 to the call controller;

FIG. 52 is a tabular representation of a SIP bye message sent to the controller from the Calgary callee;

FIG. 54 is a tabular representation of an exemplary RC call stop message;

FIG. 55 is a tabular representation of an RC call stop message for the Calgary callee;

FIG. 57 is a tabular representation of a reseller accounts table record;

FIG. 58 is a tabular representation of a reseller accounts table record for the reseller Klondike;

FIG. 59 is a tabular representation of a system operator accounts table record; and FIG. 60 is a tabular representation of a system operator accounts record for the system operator described herein.

DETAILED DESCRIPTION

Figure 1:
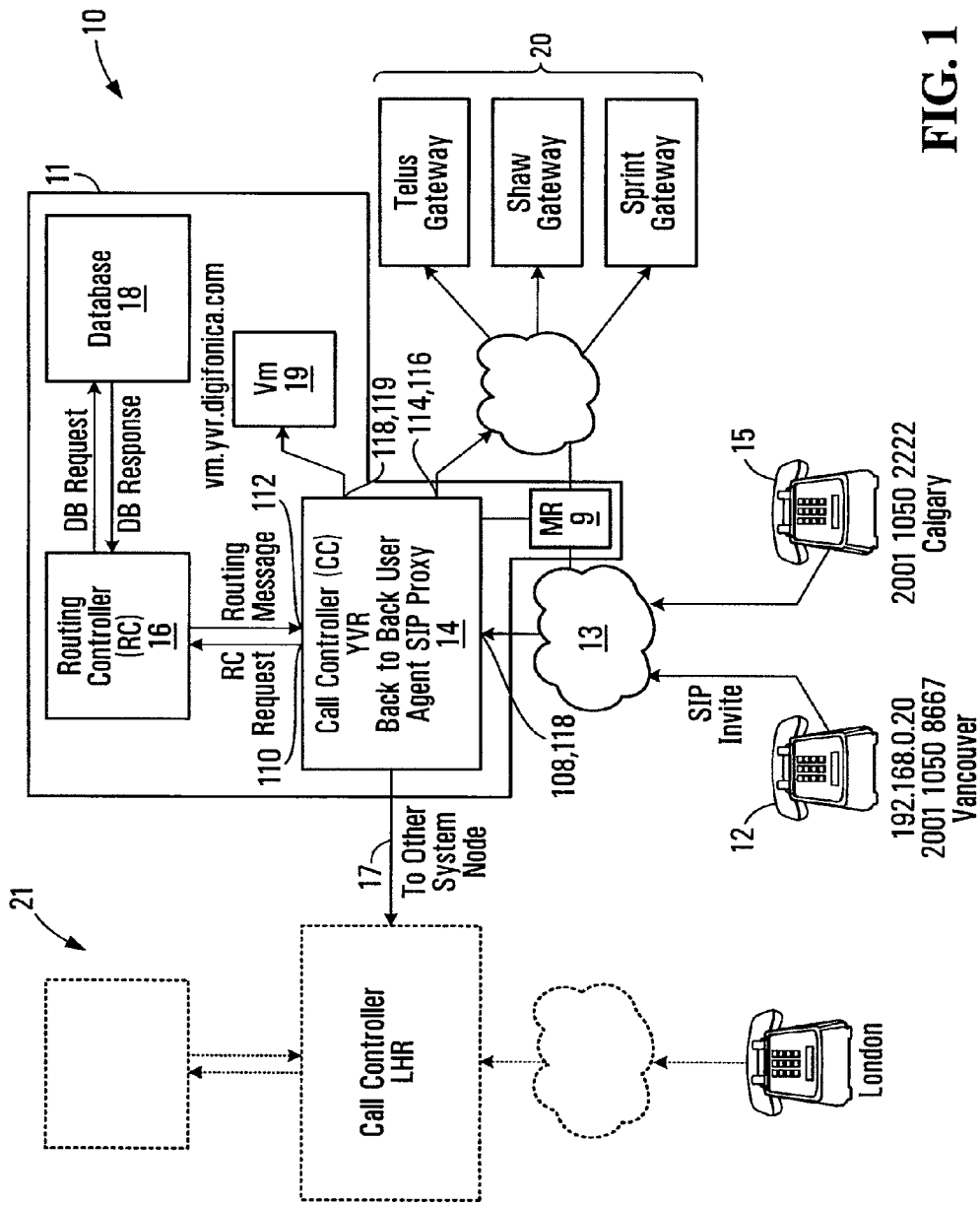
FIG. 1 is a block diagram of a system according to a first embodiment of the invention.

Referring to FIG. 1, a system for making voice over IP telephone/videophone calls is shown generally at 10. The system includes a first super node shown generally at 11 and a second super node shown generally at 21. The first super node 11 is located in geographical area, such as Vancouver, B.C., Canada for example and the second super node 21 is located in London, England, for example. Different super nodes may be located in different geographical regions throughout the world to provide telephone/videophone service to subscribers in respective regions. These super nodes may be in communication with each other by high speed/ high data throughput links including optical fiber, satellite and/or cable links, forming a backbone to the system. These super nodes may alternatively or, in addition, be in communication with each other through conventional internet services.

In the embodiment shown, the Vancouver supernode 11 provides telephone/videophone service to western Canadian customers from Vancouver Island to Ontario. Another node (not shown) may be located in Eastern Canada to provide services to subscribers in that area.

Other nodes of the type shown may also be employed within the geographical area serviced by a supernode, to provide for call load sharing, for example within a region of the geographical area serviced by the supernode. However, in general, all nodes are similar and have the properties described below in connection with the Vancouver supernode 11.

In this embodiment, the Vancouver supernode includes a call controller (C) 14, a routing controller (RC) 16, a database 18 and a voicemail server 19 and a media relay 9. Each of these may be implemented as separate modules on a common computer system or by separate computers, for example. The voicemail server 19 need not be included in the node and can be provided by an outside service provider.

Subscribers such as a subscriber in Vancouver and a subscriber in Calgary communicate with the Vancouver supernode using their own internet service providers which route internet traffic from these subscribers over the internet shown generally at 13 in FIG. 1. To these subscribers the Vancouver supernode is accessible at a pre-determined internet protocol (IP) address or a fully qualified domain name that can be accessed in the usual way through a subscriber's internet service provider. The subscriber in Vancouver uses a telephone 12 that is capable of communicating with the Vancouver supernode 11 using Session Initiation Protocol (SIP) messages and the Calgary subscriber uses a similar telephone 15, in Calgary AB.

It should be noted that throughout the description of the embodiments of this invention, the IP/UDP addresses of all elements such as the caller and callee telephones, call controller, media relay, and any others, will be assumed to be valid IP/UDP addresses directly accessible via the Internet or a private IP network, for example, depending on the specific implementation of the system. As such, it will be assumed, for example, that the caller and callee telephones will have IP/UDP addresses directly accessible by the call controllers and the media relays on their respective supernodes, and those addresses will not be obscured by Network Address Translation (NAT) or similar mechanisms. In other words, the IP/UDP information contained in SIP messages (for example the SIP Invite message or the RC Request message which will be described below) will match the IP/UDP addresses of the IP packets carrying these SIP messages.

It will be appreciated that in many situations, the IP addresses assigned to various elements of the system may be in a private IP address space, and thus not directly accessible from other elements. Furthermore, it will also be appreciated that NAT is commonly used to share a "public" IP address between multiple devices, for example between home PCs and IP telephones sharing a single Internet connection. For example, a home PC may be assigned an IP address such as 192.168.0.101 and a Voice over IP telephone may be assigned an IP address of 192.168.0.103. These addresses are located in so called "non-routable" (IP) address space and cannot be accessed directly from the Internet. In order for these devices to communicate with other computers located on the Internet, these IP addresses have to be converted into a "public" IP address, for example 24.10.10.123 assigned by the Internet Service Provider to the subscriber, by a device performing NAT, typically a home router. In addition to translating the IP addresses, NAT typically also translates UDP port numbers, for example an audio path originating at a VoIP telephone and using a UDP port 12378 at its private IP address, may have be translated to a UDP port 23465 associated with the public IP address of the NAT device. In other words, when a packet originating from the above VoIP telephone arrives at an Internet-based supernode, the source IP/UDP address contained in the IP packet header will be 24.10.10.1:23465, whereas the source IP/UDP address information contained in the SIP message inside this IP packet will be 192.168.0.103:12378. The mismatch in the IP/UDP addresses may cause a problem for SIP-based VoIP systems because, for example, a supernode will attempt to send messages to a private address of a telephone but the messages will never get there.

Referring to FIG. 1, in an attempt to make a call by the Vancouver telephone/videophone 12 to the Calgary telephone/videophone 15, the Vancouver telephone/videophone sends a SIP invite message to the Vancouver supernode 11 and in response, the call controller 14 sends an RC request message to the RC 16 which makes various enquiries of the database 18 to produce a routing message which is sent back to the call controller 14. The call controller 14 then communicates with the media relay 9 to cause a communications link including an audio path and a videophone (if a videopath call) to be established through the media relay to the same node, a different node or to a communications supplier gateway as shown generally at 20 to carry audio, and where applicable, video traffic to the call recipient or callee.

Generally, the RC 16 executes a process to facilitate communication between callers and callees. The process involves, in response to initiation of a call by a calling subscriber, receiving a callee identifier from the calling subscriber, using call classification criteria associated with the calling subscriber to classify the call as a public network call or a private network call and producing a routing message identifying an address on the private network, associated with the callee when the call is classified as a private network call and producing a routing message identifying a gateway to the public network when the call is classified as a public network call.

Subscriber Telephone

Figure 2:
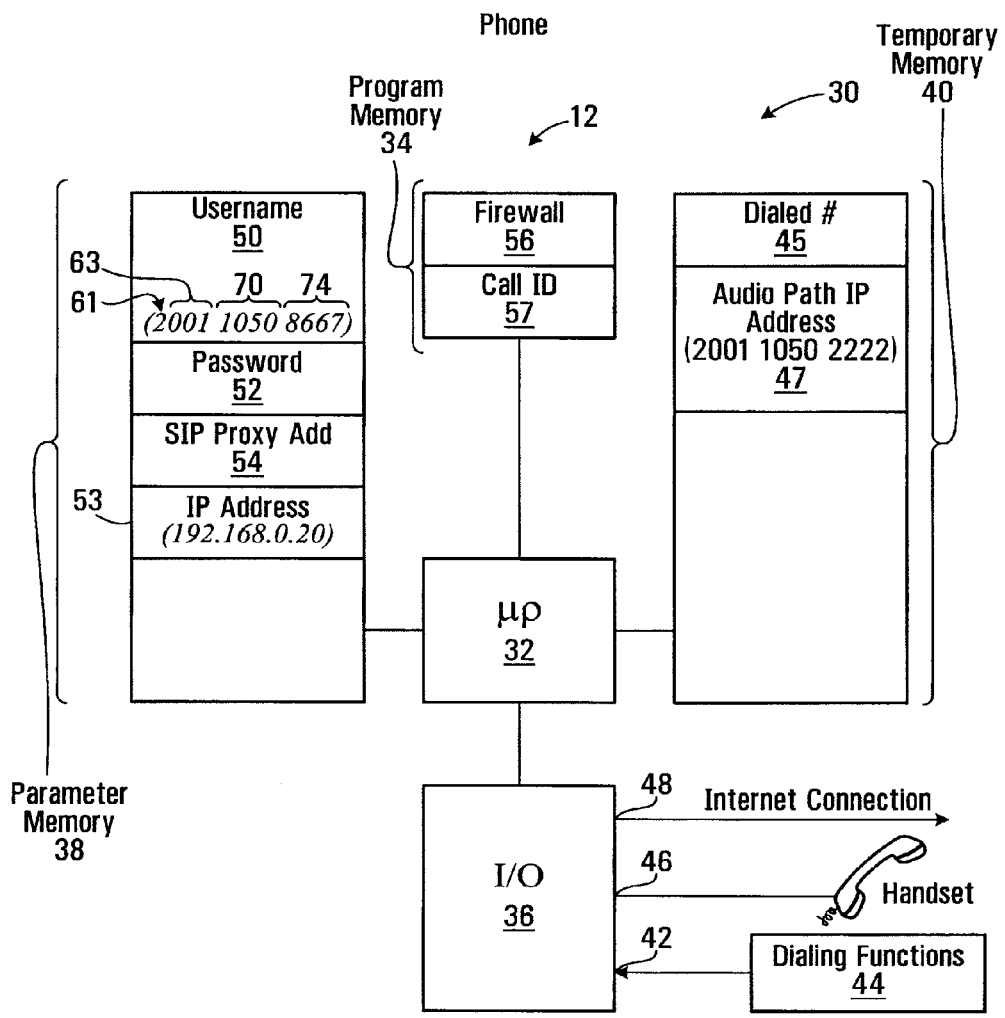
FIG. 2 is a block diagram of a caller telephone according to the first embodiment of the invention.

In greater detail, referring to FIG. 2, in this embodiment, the telephone/videophone 12 includes a processor circuit shown generally at 30 comprising a microprocessor 32, program memory 34, an input/output (I/O) port 36, parameter memory 38 and temporary memory 40. The program memory 34, I/O port 36, parameter memory 38 and temporary memory 40 are all in communication with the microprocessor 32. The I/O port 36 has a dial input 42 for receiving a dialled telephone/videophone number from a keypad, for example, or from a voice recognition unit or from pre-stored telephone/videophone numbers stored in the parameter memory 38, for example. For simplicity, in FIG. 2 a box labelled dialing functions 44 represents any device capable of informing the microprocessor 32 of a callee identifier, e.g., a callee telephone/videophone number.

The processor 32 stores the callee identifier in a dialled number buffer 45. In this case, assume the dialled number is 2001 1050 2222 and that it is a number associated with the Calgary subscriber. The I/O port 36 also has a handset interface 46 for receiving and producing signals from and to a handset that the user may place to his ear. This interface 46 may include a BLUETOOTH™ wireless interface, a wired interface or speaker phone, for example. The handset acts as a termination point for an audio path (not shown) which will be appreciated later. The I/O port 36 also has an internet connection 48 which is preferably a high speed internet connection and is operable to connect the telephone/videophone to an internet service provider. The internet connection 48 also acts as a part of the voice path, as will be appreciated later. It will be appreciated that where the subscriber device is a videophone, a separate video path is established in the same way an audio path is established. For simplicity, the following description refers to a telephone call, but it is to be understood that a videophone call is handled similarly, with the call controller causing the media relay to facilitate both an audio path and a video path instead of only an audio path.

The parameter memory 38 has a username field 50, a password field 52 an IP address field 53 and a SIP proxy address field 54, for example. The user name field 50 is operable to hold a user name, which in this case is 2001 1050 8667. The user name is assigned upon subscription or registration into the system and, in this embodiment, includes a twelve digit number having a continent code 61, a country code 63, a dealer code 70 and a unique number code 74. The continent code 61 is comprised of the first or left-most digit of the user name in this embodiment. The country code 63 is comprised of the next three digits. The dealer code 70 is comprised of the next four digits and the unique number code 74 is comprised of the last four digits. The password field 52 holds a password of up to 512 characters, in this example. The IP address field 53 stores an IP address of the telephone, which for this explanation is 192.168.0.20. The SIP proxy address field 54 holds an IP protocol compatible proxy address which may be provided to the telephone through the internet connection 48 as part of a registration procedure.

The program memory 34 stores blocks of codes for directing the processor 32 to carry out the functions of the telephone, one of which includes a firewall block 56 which provides firewall functions to the telephone, to prevent access by unauthorized persons to the microprocessor 32 and memories 34, 38 and 40 through the internet connection 48. The program memory 34 also stores codes 57 for establishing a call ID. The call ID codes 57 direct the processor 32 to produce a call identifier having a format comprising a hexadecimal string at an IP address, the IP address being the IP address of the telephone. Thus, an exemplary call identifier might be FF10@192.168.0.20.

Figures 3, 4:
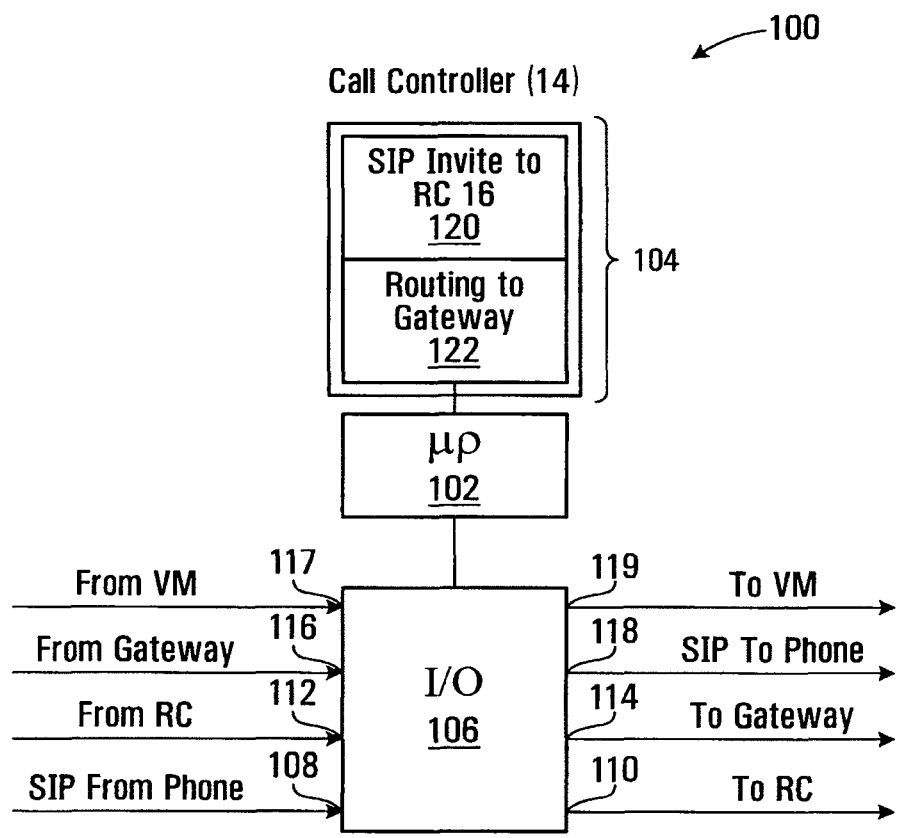
FIG. 3 is a schematic representation of a SIP invite message transmitted between the caller telephone and a controller shown in FIG. 1.
FIG. 4 is a block diagram of a call controller shown in FIG. 1.

Generally, in response to picking up the handset interface 46 and activating a dialing function 44, the microprocessor 32 produces and sends a SIP invite message as shown in FIG. 3, to the routing controller 16 shown in FIG. 1. This SIP invite message is essentially to initiate a call by a calling subscriber.

Referring to FIG. 3, the SIP invite message includes a caller ID field 60, a callee identifier field 62, a digest parameters field 64, a call ID field 65 an IP address field 67 and a caller UDP port field 69. In this embodiment, the caller ID field 60 includes the user name 2001 10508667 that is the Vancouver user name stored in the user name field 50 of the parameter memory 38 in the telephone 12 shown in FIG. 2. In addition, referring back to FIG. 3, the callee identifier field 62 includes a callee identifier which in this embodiment is the user name 2001 1050 2222 that is the dialled number of the Calgary subscriber stored in the dialled number buffer 45 shown in FIG. 2. The digest parameters field 64 includes digest parameters and the call ID field 65 includes a code comprising a generated prefix code (FF10) and a suffix which is the Internet Protocol (IP) address of the telephone 12 stored in the IP address field 53 of the telephone. The IP address field 67 holds the IP address assigned to the telephone, in this embodiment 192.168.0.20, and the caller UDP port field 69 includes a UDP port identifier identifying a UDP port at which the audio path will be terminated at the caller's telephone.

Call Controller

Referring to FIG. 4, a call controller circuit of the call controller 14 (FIG. 1) is shown in greater detail at 100. The call controller circuit 100 includes a microprocessor 102, program memory 104 and an I/O port 106. The circuit 100 may include a plurality of microprocessors, a plurality of program memories and a plurality of I/O ports to be able to handle a large volume of calls. However, for simplicity, the call controller circuit 100 will be described as having only one microprocessor 102, program memory 104 and I/O port 106, it being understood that there may be more.

Generally, the I/O port 106 includes an input 108 for receiving messages such as the SIP invite message shown in FIG. 3, from the telephone shown in FIG. 2. The I/O port 106 also has an RC request message output 110 for transmitting an RC request message to the RC 16 of FIG. 1, an RC message input 112 for receiving routing messages from the RC 16, a gateway output 114 for transmitting messages to one of the gateways 20 shown in FIG. 1 to advise the gateway to establish an audio path, for example, and a gateway input 116 for receiving messages from the gateway. The I/O port 106 further includes a SIP output 118 for transmitting messages to the telephone 12 to advise the telephone of the IP addresses of the gateways which will establish the audio path. The I/O port 106 further includes a voicemail server input and output 117, 119 respectively for communicating with the voicemail server 19 shown in FIG. 1.

While certain inputs and outputs have been shown as separate, it will be appreciated that some may be a single IP address and IP port. For example, the messages sent to the RC 16 and received from the RC 16 may be transmitted and received on the same single IP port.

The program memory 104 includes blocks of code for directing the microprocessor 102 to carry out various functions of the call controller 14. For example, these blocks of code include a first block 120 for causing the call controller circuit 100 to execute a SIP invite to RC request process to produce an RC request message in response to a received SIP invite message. In addition, there is a routing message to gateway message block 122 which causes the call controller circuit 100 to produce a gateway query message in response to a received routing message from the RC 16.

Figure 5:
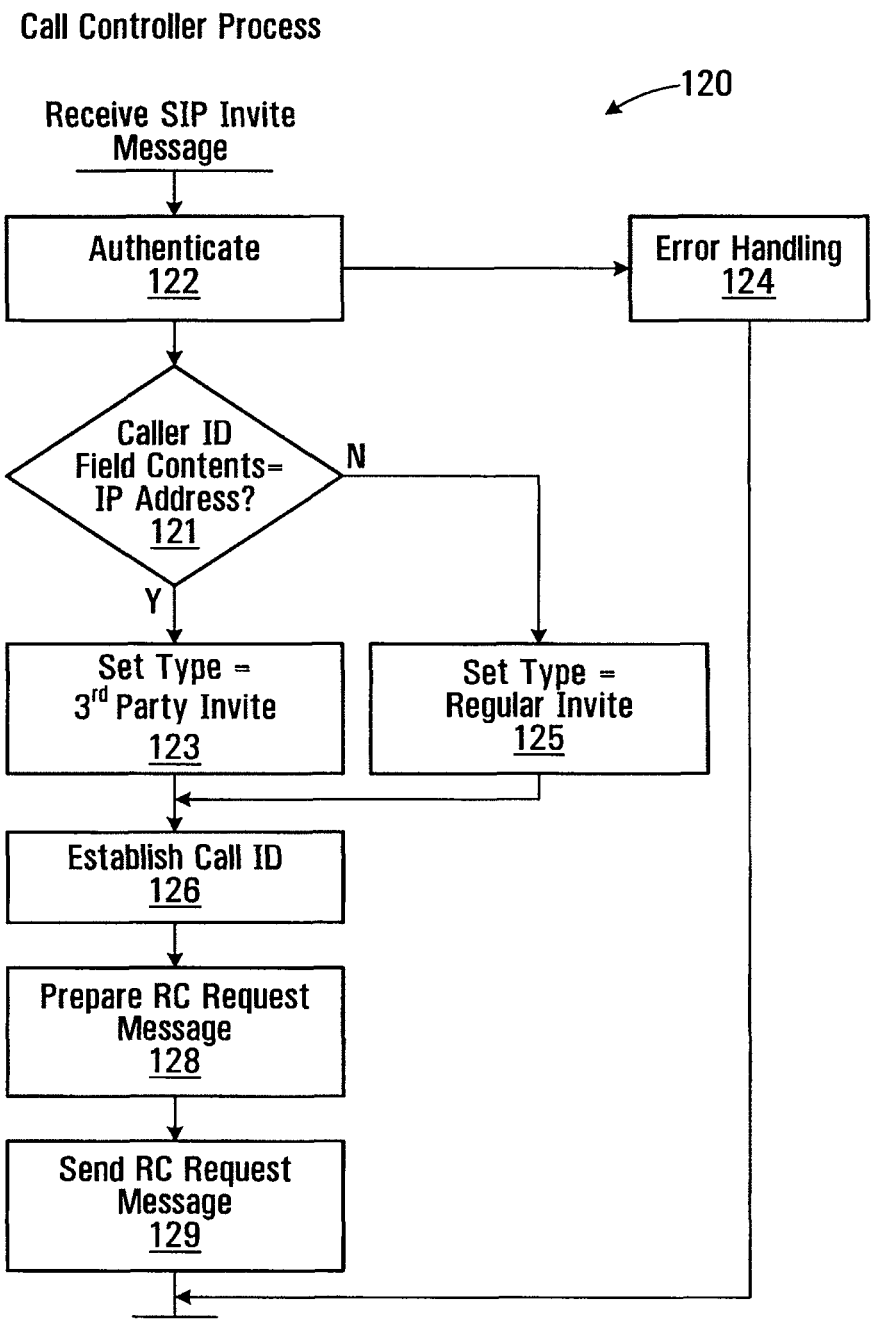
FIG. 5 is a flowchart of a process executed by the call controller shown in FIG. 1.

Referring to FIG. 5, the SIP invite to RC request process is shown in more detail at 120. On receipt of a SIP invite message of the type shown in FIG. 3, block 122 of FIG. 5 directs the call controller circuit 100 of FIG. 4 to authenticate the user. This may be done, for example, by prompting the user for a password, by sending a message back to the telephone 12 which is interpreted at the telephone as a request for a password entry or the password may automatically be sent to the call controller 14 from the telephone, in response to the message. The call controller 14 may then make enquiries of databases to which it has access, to determine whether or not the user's password matches a password stored in the database. Various functions may be used to pass encryption keys or hash codes back and forth to ensure that the transmittal of passwords is secure.

Should the authentication process fail, the call controller circuit 100 is directed to an error handling routine 124 which causes messages to be displayed at the telephone 12 to indicate there was an authentication problem. If the authentication procedure is passed, block 121 directs the call controller circuit 100 to determine whether or not the contents of the caller ID field 60 of the SIP invite message received from the telephone is an IP address. If it is an IP address, then block 123 directs the call controller circuit 100 to set the contents of a type field variable maintained by the microprocessor 102 to a code representing that the call type is a third party invite. If at block 121 the caller ID field contents do not identify an IP address, then block 125 directs the microprocessor to set the contents of the type field to a code indicating that the call is being made by a system subscriber. Then, block 126 directs the call controller circuit to read the call identifier 65 provided in the SIP invite message from the telephone 12, and at block 128 the processor is directed to produce an RC request message that includes that call ID. Block 129 then directs the call controller circuit 100 to send the RC request to the RC 16.

Figures 6, 7:
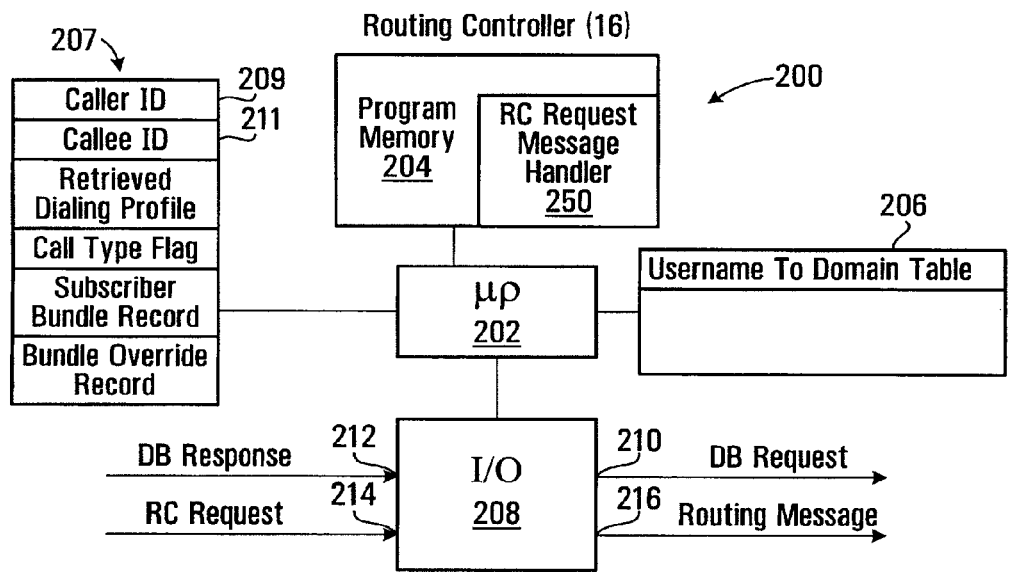
FIG. 6 is a schematic representation of a routing, billing and rating (RC) request message produced by the call controller shown in FIG. 1.
FIG. 7 is a block diagram of a processor circuit of a routing, billing, rating element of the system shown in FIG. 1.

Referring to FIG. 6, an RC request message is shown generally at 150 and includes a caller field 152, a callee field 154, a digest field 156, a call ID field 158 and a type field 160. The caller, callee, digest call ID fields 152, 154, 156 and 158 contain copies of the caller, callee, digest parameters and call ID fields 60, 62, 64 and 65 of the SIP invite message shown in FIG. 3. The type field 160 contains the type code established at blocks 123 or 125 of FIG. 5 to indicate whether the call is from a third party or system subscriber, respectively. The caller identifier field may include a PSTN number or a system subscriber username as shown, for example.

Routing Controller (RC)

Referring to FIG. 7, the RC 16 is shown in greater detail and includes an RC processor circuit shown generally at 200. The RC processor circuit 200 includes a processor 202, program memory 204, a table memory 206, buffer memory 207, and an I/O port 208, all in communication with the processor 202. (As earlier indicated, there may be a plurality of processor circuits (202), memories (204), etc.)

The buffer memory 207 includes a caller id buffer 209 and a callee id buffer 211.

The I/O port 208 includes a database request port 210 through which a request to the database (18 shown in FIG. 1) can be made and includes a database response port 212 for receiving a reply from the database 18. The I/O port 208 further includes an RC request message input 214 for receiving the RC request message from the call controller (14 shown in FIG. 1) and includes a routing message output 216 for sending a routing message back to the call controller 14. The I/O port 208 thus acts to receive caller identifier and a callee identifier contained in the RC request message from the call controller, the RC request message being received in response to initiation of a call by a calling subscriber.

The program memory 204 includes blocks of codes for directing the processor 202 to carry out various functions of the RC (16). One of these blocks includes an RC request message handler 250 which directs the RC to produce a routing message in response to a received RC request message. The RC request message handler process is shown in greater detail at 250 in FIGS. 8A through 8D.

RC Request Message Handler

Figure 8A:
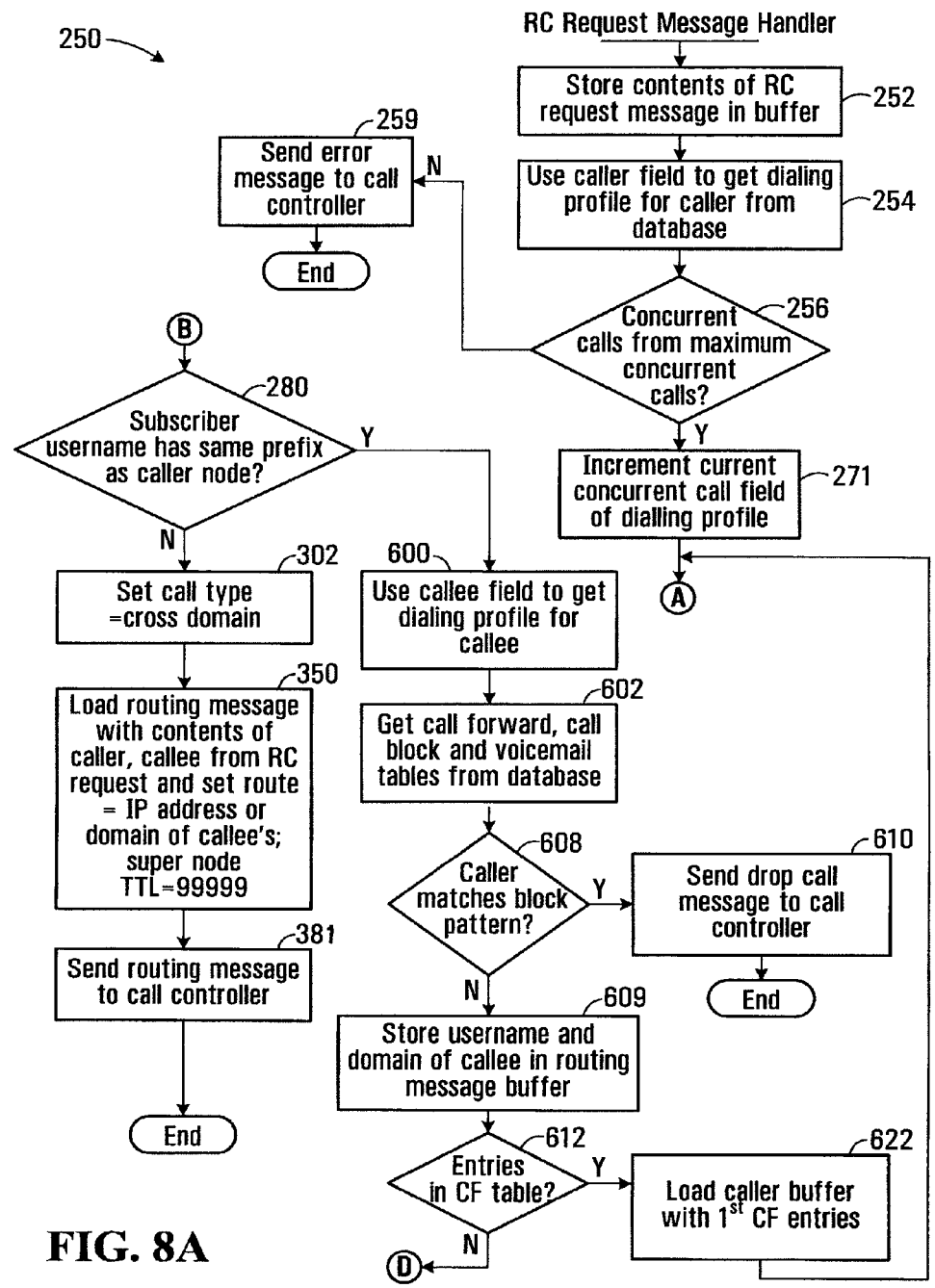
FIGS. 8A-8D is a flowchart of a RC request message handler executed by the RC processor circuit shown in FIG. 7.

Referring to FIG. 8A, the RC request message handler begins with a first block 252 that directs the RC processor circuit (200) to store the contents of the RC request message (150) in buffers in the buffer memory 207 of FIG. 7, one of which includes the caller ID buffer 209 of FIG. 7 for separately storing the contents of the callee field 154 of the RC request message. Block 254 then directs the RC processor circuit to use the contents of the caller field 152 in the RC request message shown in FIG. 6, to locate and retrieve from the database 18 a record associating calling attributes with the calling subscriber. The located record may be referred to as a dialing profile for the caller. The retrieved dialing profile may then be stored in the buffer memory 207, for example.

Referring to FIG. 9, an exemplary data structure for a dialing profile is shown generally at 253 and includes a user name field 258, a domain field 260, and calling attributes comprising a national dialing digits (NDD) field 262, an international dialing digits (IDD) field 264, a country code field 266, a local area codes field 267, a caller minimum local length field 268, a caller maximum local length field 270, a reseller field 273, a maximum number of concurrent calls field 275 and a current number of concurrent calls field 277. Effectively the dialing profile is a record identifying calling attributes of the caller identified by the caller identifier. More generally, dialing profiles represent calling attributes of respective subscribers.

An exemplary caller profile for the Vancouver subscriber is shown generally at 276 in FIG. 10 and indicates that the user name field 258 includes the user name (2001 1050 8667) that has been assigned to the subscriber and is stored in the user name field 50 in the telephone as shown in FIG. 2.

Referring back to FIG. 10, the domain field 260 includes a domain name as shown at 282, including a node type identifier 284, a location code identifier 286, a system provider identifier 288 and a domain portion 290. The domain field 260 effectively identifies a domain or node associated with the user identified by the contents of the user name field 258.

In this embodiment, the node type identifier 284 includes the code "sp" identifying a supernode and the location identifier 286 identifies the supernode as being in Vancouver (YVR). The system provider identifier 288 identifies the company supplying the service and the domain portion 290 identifies the "com" domain.

The national dialled digit field 262 in this embodiment includes the digit "1" and, in general, includes a number specified by the International Telecommunications Union (ITU) Telecommunications Standardization Sector (ITU-T) E. 164 Recommendation which assigns national dialing digits to countries.

The international dialing digit field 264 includes a code also assigned according to the ITU-T according to the country or location of the user.

The country code field 266 also includes the digit "1" and, in general, includes a number assigned according to the ITU-T to represent the country in which the user is located.

The local area codes field 267 includes a list of area codes that have been assigned by the ITU-T to the geographical area in which the subscriber is located. The caller minimum and maximum local number length fields 268 and 270 hold numbers representing minimum and maximum local number lengths permitted in the area code(s) specified by the contents of the local area codes field 267. The reseller field 273 is optional and holds a code identifying a retailer of the services, in this embodiment "Klondike". The maximum number of concurrent calls field 275 holds a code identifying the maximum number of concurrent calls that the user is entitled to cause to concurrently exist. This permits more than one call to occur concurrently while all calls for the user are billed to the same account. The current number of concurrent calls field 277 is initially 0 and is incremented each time a concurrent call associated with the user is initiated and is decremented when a concurrent call is terminated.

The area codes associated with the user are the area codes associated with the location code identifier 286 of the contents of the domain field 260.

A dialing profile of the type shown in FIG. 9 is produced whenever a user registers with the system or agrees to become a subscriber to the system. Thus, for example, a user wishing to subscribe to the system may contact an office maintained by a system operator and personnel in the office may ask the user certain questions about his location and service preferences, whereupon tables can be used to provide office personnel with appropriate information to be entered into the user name 258, domain 260, NDD 262, IDD 264, country code 266, local area codes 267, caller minimum and maximum local length fields 268 and 270 reseller field 273 and concurrent call fields 275 and 277 to establish a dialing profile for the user.

Referring to FIGS. 11 and 12, callee dialing profiles for users in Calgary and London, respectively for example, are shown.

In addition to creating dialing profiles when a user registers with the system, a direct-in-dial (DID) record of the type shown at 278 in FIG. 13 is added to a direct-in-dial bank table in the database (18 in FIG. 1) to associate the username and a host name of the supernode with which the user is associated, with an E.164 number associated with the user on the PSTN network.

An exemplary DID table record entry for the Calgary callee is shown generally at 300 in FIG. 14. The user name field 281 and user domain field 272 are analogous to the user name and user domain fields 258 and 260 of the caller dialing profile shown in FIG. 10. The contents of the DID field 274 include a E.164 public telephone number including a country code 283, an area code 285, an exchange code 287 and a number 289. If the user has multiple telephone numbers, then multiple records of the type shown at 300 would be included in the DID bank table, each having the same user name and user domain, but different DID field 274 contents reflecting the different telephone numbers associated with that user.

In addition to creating dialing profiles as shown in FIG. 9 and DID records as shown in FIG. 13 when a user registers with the system, call blocking records of the type shown in FIG. 26, call forwarding records of the type shown in FIG. 28 and voicemail records of the type shown in FIG. 30 may be added to the database 18 when a new subscriber is added to the system.

Referring back to FIG. 8A, after retrieving a dialing profile for the caller, such as shown at 276 in FIG. 10, the RC processor circuit 200 is directed to block 256 which directs the processor circuit (200) to determine whether the contents of the concurrent call field 277 are less then the contents of the maximum concurrent call field 275 of the dialing profile for the caller and, if so, block 271 directs the processor circuit to increment the contents of the concurrent call field 277. If the contents of concurrent call field 277 are equal to or greater than the contents of the maximum concurrent call field 275, block 259 directs the processor circuit 200 to send an error message back to the call controller (14) to cause the call controller to notify the caller that the maximum number of concurrent calls has been reached and no further calls can exist concurrently, including the presently requested call.

Assuming block 256 allows the call to proceed, the RC processor circuit 200 is directed to perform certain checks on the callee identifier provided by the contents of the callee field 154 in FIG. 6, of the RC request message 150. These checks are shown in greater detail in FIG. 8B.

Figure 8B:
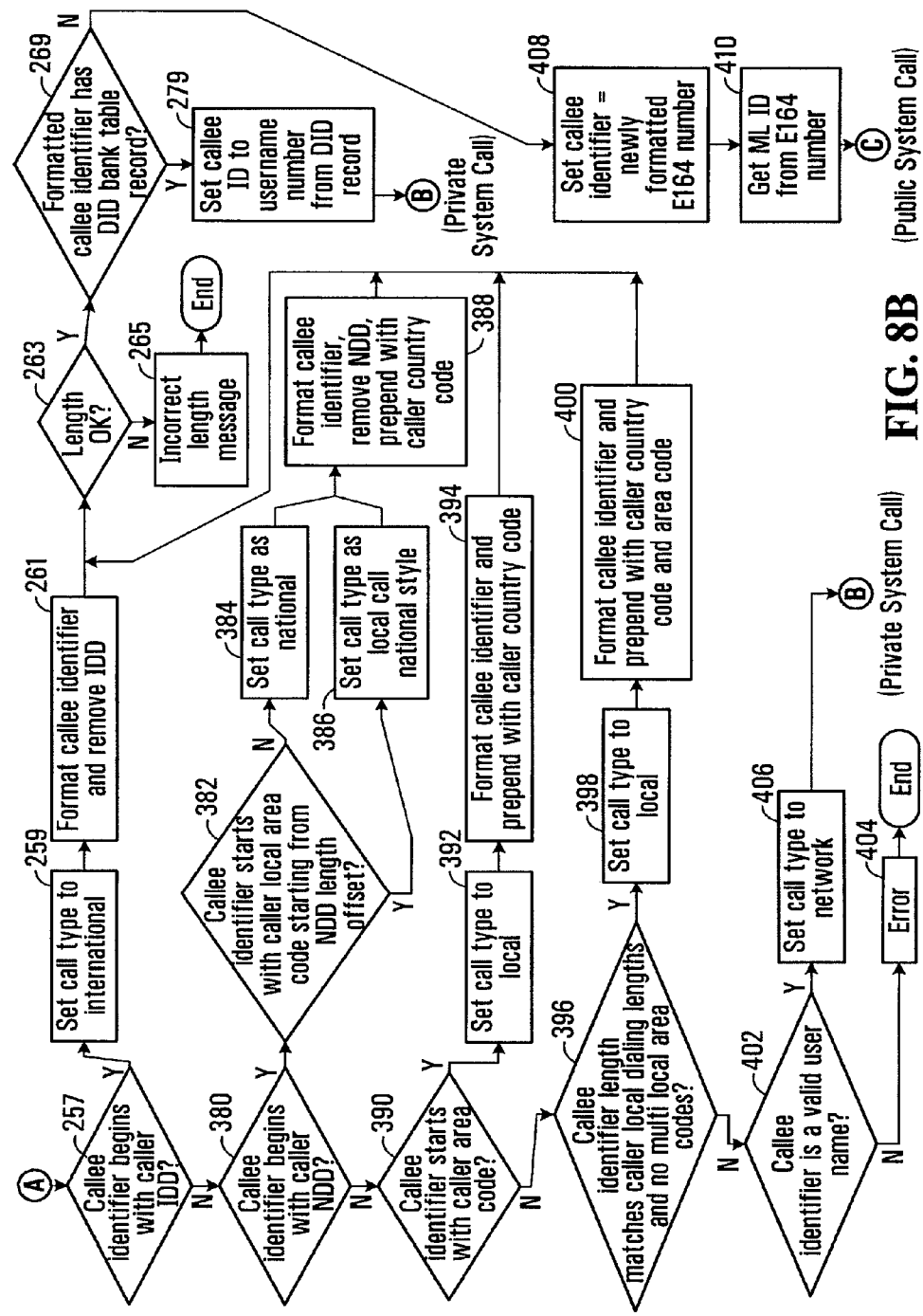

Referring to FIG. 8B, the processor (202 in FIG. 7) is directed to a first block 257 that causes it to determine whether a digit pattern of the callee identifier (154) provided in the RC request message (150) includes a pattern that matches the contents of the international dialing digits (IDD) field 264 in the caller profile shown in FIG. 10. If so, then block 259 directs the processor (202) to set a call type code identifier variable maintained by the processor to indicate that the call is an international call and block 261 directs the processor to produce a reformatted callee identifier by reformatting the callee identifier into a predefined digit format. In this embodiment, this is done by removing the pattern of digits matching the IDD field contents 264 of the caller dialing profile to effectively shorten the callee identifier. Then, block 263 directs the processor 202 to determine whether or not the callee identifier has a length which meets criteria establishing it as a number compliant with the E.164 Standard set by the ITU. If the length does not meet this criteria, block 265 directs the processor 202 to send back to the call controller (14) a message indicating the length is not correct. The process is then ended. At the call controller 14, routines (not shown) stored in the program memory 104 may direct the processor (102 of FIG. 4) to respond to the incorrect length message by transmitting a message back to the telephone (12 shown in FIG. 1) to indicate that an invalid number has been dialled.

Still referring to FIG. 8B, if the length of the amended callee identifier meets the criteria set forth at block 263, block 269 directs the processor (202 of FIG. 7) to make a database request to determine whether or not the amended callee identifier is found in a record in the direct-in-dial bank (DID) table. Referring back to FIG. 8B, at block 269, if the processor 202 receives a response from the database indicating that the reformatted callee identifier produced at block 261 is found in a record in the DID bank table, then the callee is a subscriber to the system and the call is classified as a private network call by directing the processor to block 279 which directs the processor to copy the contents of the corresponding user name field (281 in FIG. 14) from the callee DID bank table record (300 in FIG. 14) into the callee ID buffer (211 in FIG. 7). Thus, the processor 202 locates a subscriber user name associated with the reformatted callee identifier. The processor 202 is then directed to point B in FIG. 8A.

Subscriber to Subscriber Calls Between Different Nodes

Referring to FIG. 8A, block 280 directs the processor (202 of FIG. 7) to execute a process to determine whether or not the node associated with the reformatted callee identifier is the same node that is associated with the caller identifier. To do this, the processor 202 determines whether or not a prefix (e.g., continent code 61) of the callee name held in the callee ID buffer (211 in FIG. 7), is the same as the corresponding prefix of the caller name held in the username field 258 of the caller dialing profile shown in FIG. 10. If the corresponding prefixes are not the same, block 302 in FIG. 8A directs the processor (202 in FIG. 7) to set a call type flag in the buffer memory (207 in FIG. 7) to indicate the call is a cross-domain call. Then, block 350 of FIG. 8A directs the processor (202 of FIG. 7) to produce a routing message identifying an address on the private network with which the callee identified by the contents of the callee ID buffer is associated and to set a time to live for the call at a maximum value of 99999, for example.

Thus the routing message includes a caller identifier, a call identifier set according to a username associated with the located DID bank table record and includes an identifier of a node on the private network with which the callee is associated.

The node in the system with which the callee is associated is determined by using the callee identifier to address a supernode table having records of the type as shown at 370 in FIG. 17. Each record 370 has a prefix field 372 and a supernode address field 374. The prefix field 372 includes the first n digits of the callee identifier. In this embodiment, n=2. The supernode address field 374 holds a code representing the IP address or a fully qualified domain name of the node associated with the code stored in the callee identifier prefix field 372. Referring to FIG. 18, for example, if the prefix is 20, the supernode address associated with that prefix is sp.yvr.digifonica.com.

Referring to FIG. 15, a generic routing message is shown generally at 352 and includes an optional supplier prefix field 354, and optional delimiter field 356, a callee user name field 358, at least one route field 360, a time to live field 362 and other fields 364. The optional supplier prefix field 354 holds a code for identifying supplier traffic. The optional delimiter field 356 holds a symbol that delimits the supplier prefix code from the callee user name field 358. In this embodiment, the symbol is a number sign (#). The route field 360 holds a domain name or IP address of a gateway or node that is to carry the call, and the time to live field 362 holds a value representing the number of seconds the call is permitted to be active, based on subscriber available minutes and other billing parameters.

Referring to FIG. 8A and FIG. 16, an example of a routing message produced by the processor at block 350 for a caller associated with a different node than the caller is shown generally at 366 and includes only a callee field 359, a route field 361 and a time to live field 362.

Referring to FIG. 8A, having produced a routing message as shown in FIG. 16, block 381 directs the processor (202 of FIG. 7) to send the routing message shown in FIG. 16 to the call controller 14 shown in FIG. 1.

Referring back to FIG. 8B, if at block 257, the callee identifier stored in the callee id buffer (211 in FIG. 7) does not begin with an international dialing digit, block 380 directs the processor (202) to determine whether or not the callee identifier begins with the same national dial digit code as assigned to the caller. To do this, the processor (202) is directed to refer to the retrieved caller dialing profile as shown in FIG. 10. In FIG. 10, the national dialing digit code 262 is the number 1. Thus, if the callee identifier begins with the number 1, then the processor (202) is directed to block 382 in FIG. 8B.

Block 382 directs the processor (202 of FIG. 7) to examine the callee identifier to determine whether or not the digits following the NDD digit identify an area code that is the same as any of the area codes identified in the local area codes field 267 of the caller dialing profile 276 shown in FIG. 10. If not, block 384 of FIG. 8B directs the processor 202 to set the call type flag to indicate that the call is a national call. If the digits following the NDD digit identify an area code that is the same as a local area code associated with the caller as indicated by the caller dialing profile, block 386 directs the processor 202 to set the call type flag to indicate a local call, national style. After executing blocks 384 or 386, block 388 directs the processor 202 to format the callee identifier into a pre-defined digit format to produce a re-formatted callee identifier by removing the national dialled digit and prepending a caller country code identified by the country code field 266 of the caller dialing profile shown in FIG. 10. The processor (202) is then directed to block 263 of FIG. 8B to perform other processing as already described above.

If at block 380, the callee identifier does not begin with a national dialled digit, block 390 directs the processor (202) to determine whether the callee identifier begins with digits that identify the same area code as the caller. Again, the reference for this is the retrieved caller dialing profile shown in FIG. 10. The processor (202) determines whether or not the first few digits of the callee identifier identify an area code corresponding to the local area code field 267 of the retrieved caller dialing profile. If so, then block 392 directs the processor 202 to set the call type flag to indicate that the call is a local call and block 394 directs the processor (202) to format the callee identifier into a pre-defined digit format to produce a reformatted callee identifier by prepending the caller country code to the callee identifier, the caller country code being determined from the country code field 266 of the retrieved caller dialing profile shown in FIG. 10. The processor (202) is then directed to block 263 for further processing as described above.

Referring back to FIG. 8B, at block 390, the callee identifier does not start with the same area code as the caller, block 396 directs the processor (202 of FIG. 7) to determine whether the number of digits in the callee identifier, i.e. the length of the callee identifier, is within the range of digits indicated by the caller minimum local number length field 268 and the caller maximum local number length field 270 of the retrieved caller dialing profile shown in FIG. 10. If so, then block 398 directs the processor (202) to set the call type flag to indicate a local call and block 400 directs the processor (202) to format the callee identifier into a pre-defined digit format to produce a reformatted callee identifier by prepending to the callee identifier the caller country code (as indicated by the country code field 266 of the retrieved caller dialing profile shown in FIG. 10) followed by the caller area code (as indicated by the local area code field 267 of the caller profile shown in FIG. 10). The processor (202) is then directed to block 263 of FIG. 8B for further processing as described above.

Referring back to FIG. 8B, if at block 396, the callee identifier has a length that does not fall within the range specified by the caller minimum local number length field (268 in FIG. 10) and the caller maximum local number length field (270 in FIG. 10), block 402 directs the processor 202 of FIG. 7 to determine whether or not the callee identifier identifies a valid user name. To do this, the processor 202 searches through the database (18 of FIG. 10 of dialing profiles to find a dialing profile having user name field contents (258 in FIG. 10) that match the callee identifier. If no match is found, block 404 directs the processor (202) to send an error message back to the call controller (14). If at block 402, a dialing profile having a user name field 258 that matches the callee identifier is found, block 406 directs the processor 202 to set the call type flag to indicate that the call is a private network call and then the processor is directed to block 280 of FIG. 8A. Thus, the call is classified as a private network call when the callee identifier identifies a subscriber to the private network.

From FIG. 8B, it will be appreciated that there are certain groups of blocks of codes that direct the processor 202 in FIG. 7 to determine whether the callee identifier has certain features such as an international dialing digit, a national dialing digit, an area code and a length that meet certain criteria, and cause the processor 202 to reformat the callee identifier stored in the callee id buffer 211, as necessary into a predetermined target format including only a country code, area code, and a normal telephone number, for example, to cause the callee identifier to be compatible with the E.164 number plan standard in this embodiment. This enables block 269 in FIG. 8B to have a consistent format of callee identifiers for use in searching through the DID bank table records of the type shown in FIG. 13 to determine how to route calls for subscriber to subscriber calls on the same system. Effectively, therefore blocks 257, 380, 390, 396 and 402 establish call classification criteria for classifying the call as a public network call or a private network call. Block 269 classifies the call, depending on whether or not the formatted callee identifier has a DID bank table record and this depends on how the call classification criteria are met and block 402 directs the processor 202 of FIG. 7 to classify the call as a private network call when the callee identifier complies with a pre-defined format, i.e. is a valid user name and identifies a subscriber to the private network, after the callee identifier has been subjected to the classification criteria of blocks 257, 380, 390 and 396.

Subscriber to Non-Subscriber Calls

Not all calls will be subscriber to subscriber calls and this will be detected by the processor 202 of FIG. 7 when it executes block 269 in FIG. 8B, and does not find a DID bank table record that is associated with the callee, in the DID bank table. When this occurs, the call is classified as a public network call by directing the processor 202 to block 408 of FIG. 8B which causes it to set the contents of the callee id buffer 211 of FIG. 7 equal to the newly formatted callee identifier, i.e., a number compatible with the E.164 standard. Then, block 410 of FIG. 8B directs the processor (202) to search a database of route or master list records associating route identifiers with dialing codes shown in FIG. 19 to locate a router having a dialing code having a number pattern matching at least a portion of the reformatted callee identifier.

Referring to FIG. 19, a data structure for a master list or route list record is shown. Each master list record includes a master list ID field 500, a dialing code field 502, a country code field 504, a national sign number field 506, a minimum length field 508, a maximum length field 510, a national dialled digit field 512, an international dialled digit field 514 and a buffer rate field 516.

The master list ID field 500 holds a unique code such as 1019, for example, identifying the record. The dialing code field 502 holds a predetermined number pattern that the processor 202 of FIG. 7 uses at block 410 in FIG. 8B to find the master list record having a dialing code matching the first few digits of the amended callee identifier stored in the callee id buffer 211. The country code field 504 holds a number representing the country code associated with the record and the national sign number field 506 holds a number representing the area code associated with the record. (It will be observed that the dialing code is a combination of the contents of the country code field 504 and the national sign number field 506.) The minimum length field 508 holds a number representing the minimum length of digits associated with the record and the maximum length field 51 holds a number representing the maximum number of digits in a number with which the record may be compared. The national dialled digit (NDD) field 512 holds a number representing an access code used to make a call within the country specified by the country code, and the international dialled digit (IDD) field 514 holds a number representing the international prefix needed to dial a call from the country indicated by the country code.

Thus, for example, a master list record may have a format as shown in FIG. 20 with exemplary field contents as shown.

Referring back to FIG. 8B, using the country code and area code portions of the reformatted callee identifier stored in the callee id buffer 211, block 410 directs the processor 202 of FIG. 7 to find a master list record such as the one shown in FIG. 20 having a dialing code that matches the country code (1) and area code (604) of the callee identifier. Thus, in this example, the processor (202) would find a master list record having an ID field containing the number 1019. This number may be referred to as a route ID. Thus, a route ID number is found in the master list record associated with a predetermined number pattern in the reformatted callee identifier.

Figure 8C:
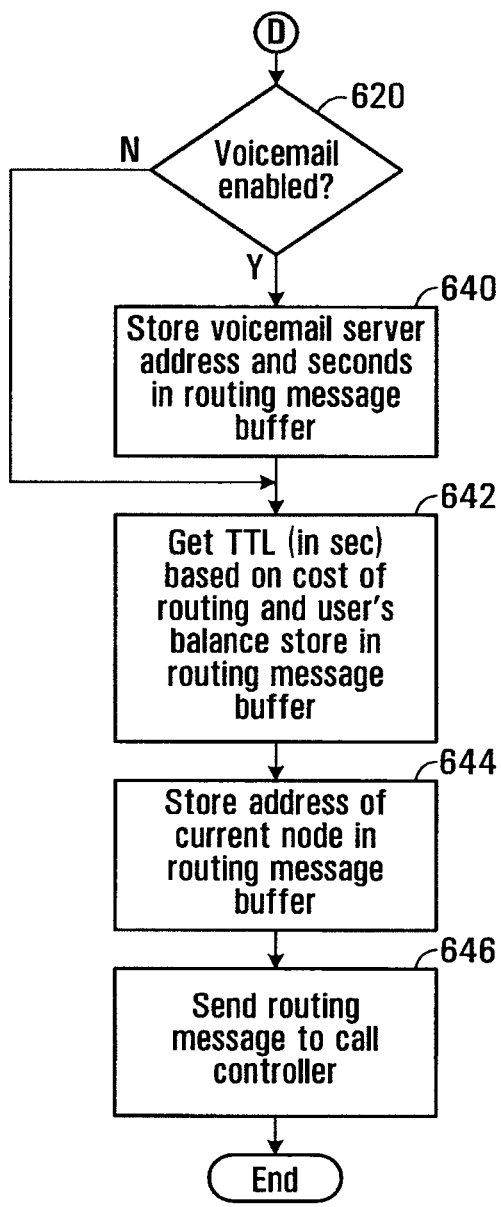
Figure 8D:
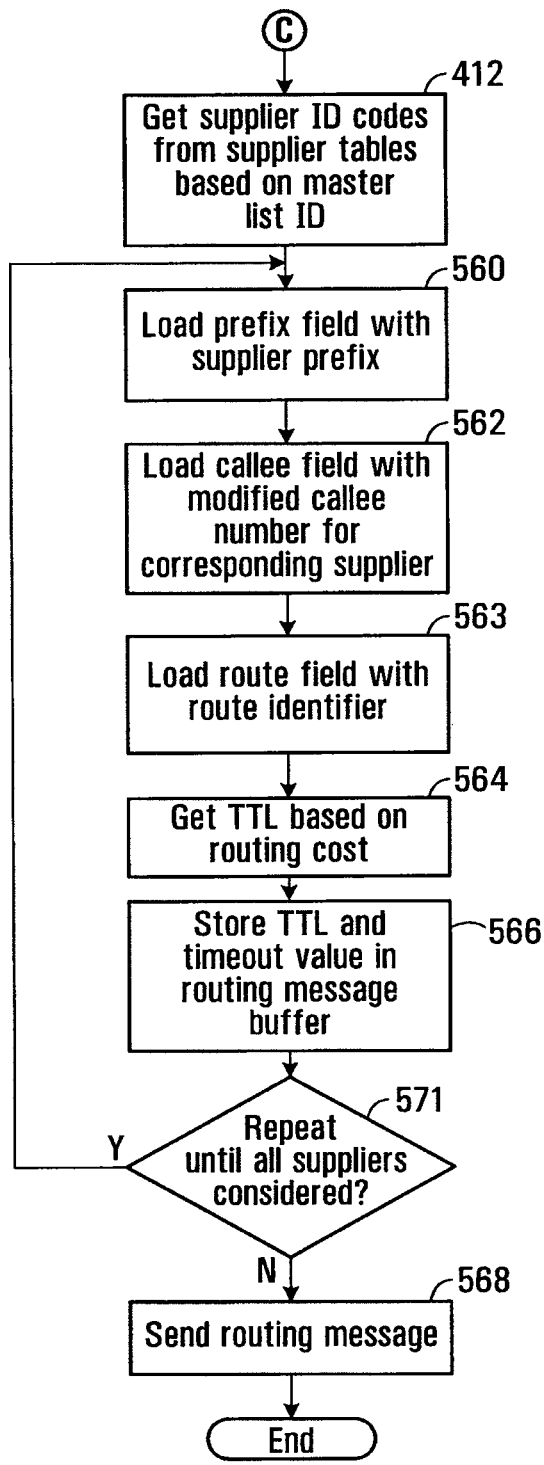

After executing block 410 in FIG. 8B, the process continues as shown in FIG. 8D. Referring to FIG. 8D, block 412 directs the processor 202 of FIG. 7 to use the route ID number to search a database of supplier records associating supplier identifiers with route identifiers to locate at least one supplier record associated with the route identifier to identify at least one supplier operable to supply a communications link for the route.

Referring to FIG. 21, a data structure for a supplier list record is shown. Supplier list records include a supplier ID field 540, a master list ID field 542, an optional prefix field 544, a specific route identifier field 546, a NDD/IDD rewrite field 548, a rate field 550, and a timeout field 551. The supplier ID field 540 holds a code identifying the name of the supplier and the master list ID field 542 holds a code for associating the supplier record with a master list record. The prefix field 544 holds a string used to identify the supplier traffic and the specific route identifier field 546 holds an IP address of a gateway operated by the supplier indicated by the supplier ID field 540. The NDD/IDD rewrite field 548 holds a code representing a rewritten value of the NDD/IDD associated with this route for this supplier, and the rate field 550 holds a code indicating the cost per second to the system operator to use the route provided by the gateway specified by the contents of the route identifier field 546. The timeout field 551 holds a code indicating a time that the call controller should wait for a response from the associated gateway before giving up and trying the next gateway. This time value may be in seconds, for example. Exemplary supplier records are shown in FIGS. 22, 23 and 24 for the exemplary suppliers shown at 20 in FIG. 1, namely Telus, Shaw and Sprint.

Referring back to FIG. 8D, at block 412 the processor 202 finds all supplier records that identify the master list ID found at block 410 of FIG. 8B.

Referring back to FIG. 8D, block 560 directs the processor 202 of FIG. 7 to begin to produce a routing message of the type shown in FIG. 15. To do this, the processor 202 loads a routing message buffer as shown in FIG. 25 with a supplier prefix of the least costly supplier where the least costly supplier is determined from the rate fields 550 of FIG. 21 of the records associated with respective suppliers.

Referring to FIGS. 22-24, in the embodiment shown, the supplier "Telus" has the lowest number in the rate field 550 and therefore the prefix 4973 associated with that supplier is loaded into the routing message buffer shown in FIG. 25 first.

Block 562 in FIG. 8D directs the processor to delimit the prefix 4973 by the number sign (#) and to next load the reformatted callee identifier into the routing message buffer shown in FIG. 25. At block 563 of FIG. 8D, the contents of the route identifier field 546 of FIG. 21 of the record associated with the supplier "Telus" are added by the processor 202 of FIG. 7 to the routing message buffer shown in FIG. 25 after an @ sign delimiter, and then block 564 in FIG. 8D directs the processor to get a time to live value, which in one embodiment may be 3600 seconds, for example. Block 566 then directs the processor 202 to load this time to live value and the timeout value (551) in FIG. 21 in the routing message buffer of FIG. 25. Accordingly, a first part of the routing message for the Telus gateway is shown generally at 570 in FIG. 25.

Referring back to FIG. 8D, block 571 directs the processor 202 back to block 560 and causes it to repeat blocks 560, 562, 563, 564 and 566 for each successive supplier until the routing message buffer is loaded with information pertaining to each supplier identified by the processor at block 412. Thus, a second portion of the routing message as shown at 572 in FIG. 25 relates to the second supplier identified by the record shown in FIG. 23. Referring back to FIG. 25, a third portion of the routing message as shown at 574 and is associated with a third supplier as indicated by the supplier record shown in FIG. 24.

Consequently, referring to FIG. 25, the routing message buffer holds a routing message identifying a plurality of different suppliers able to provide gateways to the public telephone network (i.e. specific routes) to establish at least part of a communication link through which the caller may contact the callee. In this embodiment, each of the suppliers is identified, in succession, according to rate. Other criteria for determining the order in which suppliers are listed in the routing message may include preferred supplier priorities which may be established based on service agreements, for example.

Referring back to FIG. 8D, block 568 directs the processor 202 of FIG. 7 to send the routing message shown in FIG. 25 to the call controller 14 in FIG. 1.

Subscriber to Subscriber Calls Within the Same Node

Referring back to FIG. 8A, if at block 280, the callee identifier received in the RC request message has a prefix that identifies the same node as that associated with the caller, block 600 directs the processor 202 to use the callee identifier in the callee id buffer 211 to locate and retrieve a dialing profile for the callee. The dialing profile may be of the type shown in FIG. 11 or 12, for example. Block 602 of FIG. 8A then directs the processor 202 of FIG. 7 to get call block, call forward and voicemail records from the database 18 of FIG. 1 based on the user name identified in the callee dialing profile retrieved by the processor at block 600. Call block, call forward and voicemail records may be as shown in FIGS. 26, 27, 28 and 30 for example.

Referring to FIG. 26, the call block records include a user name field 604 and a block pattern field 606. The user name field holds a user name corresponding to the user name in the user name field (258 in FIG. 10) of the callee profile and the block pattern field 606 holds one or more E.164-compatible numbers or user names identifying PSTN numbers or system subscribers from whom the subscriber identified in the user name field 604 does not wish to receive calls.

Referring to FIG. 8A and FIG. 27, block 608 directs the processor 202 of FIG. 7 to determine whether or not the caller identifier received in the RC request message matches a block pattern stored in the block pattern field 606 of the call block record associated with the callee identified by the contents of the user name field 604 in FIG. 26. If the caller identifier matches a block pattern, block 610 directs the processor to send a drop call or non-completion message to the call controller (14) and the process is ended. If the caller identifier does not match a block pattern associated with the callee, block 609 directs the processor to store the username and domain of the callee, as determined from the callee dialing profile, and a time to live value in the routing message buffer as shown at 650 in FIG. 32. Referring back to FIG. 8A, block 612 then directs the processor 202 to determine whether or not call forwarding is required.

Referring to FIG. 28, the call forwarding records include a user name field 614, a destination number field 616, and a sequence number field 618. The user name field 614 stores a code representing a user with which the record is associated. The destination number field 616 holds a user name representing a number to which the current call should be forwarded, and the sequence number field 618 holds an integer number indicating the order in which the user name associated with the corresponding destination number field 616 should be attempted for call forwarding. The call forwarding table may have a plurality of records for a given user. The processor 202 of FIG. 7 uses the contents of the sequence number field 618 to place the records for a given user in order. As will be appreciated below, this enables the call forwarding numbers to be tried in an ordered sequence.

Referring to FIG. 8A and FIG. 29, if at block 612, the call forwarding record for the callee identified by the callee identifier contains no contents in the destination number field 616 and accordingly no contents in the sequence number field 618, there are no call forwarding entries for this callee, and the processor 202 is directed to block 620 in FIG. 8C. If there are entries in the call forwarding table 27, block 622 in FIG. 8A directs the processor 202 to search the dialing profile table to find a dialing profile record as shown in FIG. 9, for the user identified by the destination number field 616 of the call forward record shown in FIG. 28. The processor 202 of FIG. 7 is further directed to store the username and domain for that user and a time to live value in the routing message buffer as shown at 652 in FIG. 32, to produce a routing message as illustrated. This process is repeated for each call forwarding record associated with the callee identified by the callee id buffer 211 in FIG. 7 to add to the routing message buffer all call forwarding usernames and domains associated with the callee.

Referring back to FIG. 8A, if at block 612 there are no call forwarding records, then at block 620 in FIG. 8C the processor 202 is directed to determine whether or not the user identified by the callee identifier has paid for voicemail service. This is done by checking to see whether or not a flag is set in a voicemail record of the type shown in FIG. 30 in a voicemail table stored in the database 18 shown in FIG. 1.

Referring to FIG. 30, voicemail records in this embodiment may include a user name field 624, a voicemail server field 626, a seconds to voicemail field 628 and an enable field 630. The user name field 624 stores the user name of the callee. The voicemail server field 626 holds a code identifying a domain name of a voicemail server associated with the user identified by the user name field 624. The seconds to voicemail field 628 holds a code identifying the time to wait before engaging voicemail, and the enable field 630 holds a code representing whether or not voicemail is enabled for the user. Referring back to FIG. 8C, at block 620 if the processor 202 of FIG. 7 finds a voicemail record as shown in FIG. 30 having user name field 624 contents matching the callee identifier, the processor is directed to examine the contents of the enabled field 630 to determine whether or not voicemail is enabled. If voicemail is enabled, then block 640 in FIG. 8C directs the processor 202 to FIG. 7 to store the contents of the voicemail server field 626 and the contents of the seconds to voicemail field 628 in the routing message buffer, as shown at 654 in FIG. 32. Block 642 then directs the processor 202 to get time to live values for each path specified by the routing message according to the cost of routing and the user's balance. These time to live values are then appended to corresponding paths already stored in the routing message buffer.

Referring back to FIG. 8C, block 644 then directs the processor 202 of FIG. 7 to store the IP address of the current node in the routing message buffer as shown at 656 in FIG. 32. Block 646 then directs the processor 202 to send the routing message shown in FIG. 32 to the call controller 14 in FIG. 1. Thus in the embodiment described the routing controller will produce a routing message that will cause at least one of the following: forward the call to another party, block the call and direct the caller to a voicemail server.

Referring back to FIG. 1, the routing message whether of the type shown in FIGS. 16, 25 or 32, is received at the call controller 14 and the call controller interprets the receipt of the routing message as a request to establish a call.

Referring to FIG. 4, the program memory 104 of the call controller 14 includes a routing to gateway routine depicted generally at 122.

Where a routing message of the type shown in FIG. 32 is received by the call controller 14, the routing to gateway routine 122 shown in FIG. 4 may direct the processor 102 cause a message to be sent back through the internet 13 shown in FIG. 1 to the callee telephone 15, knowing the IP address of the callee telephone 15 from the user name.

Alternatively, if the routing message is of the type shown in FIG. 16, which identifies a domain associated with another node in the system, the call controller may send a SIP invite message along the high speed backbone 17 connected to the other node. The other node functions as explained above, in response to receipt of a SIP invite message.

If the routing message is of the type shown in FIG. 25 where there are a plurality of gateway suppliers available, the call controller sends a SIP invite message to the first supplier, in this case Telus, using a dedicated line or an internet connection to determine whether or not Telus is able to handle the call. If the Telus gateway returns a message indicating it is not able to handle the call, the call controller 14 then proceeds to send a SIP invite message to the next supplier, in this case Shaw. The process is repeated until one of the suppliers responds indicating that it is available to carry the call. Once a supplier responds indicating that it is able to carry the call, the supplier sends back to the call controller 14 an IP address for a gateway provided by the supplier through which the call or audio path of the call will be carried. This IP address is sent in a message from the call controller 14 to the media relay 9 which responds with a message indicating an IP address to which the caller telephone should send its audio/video, traffic and an IP address to which the gateway should send its audio/video for the call. The call controller conveys the IP address at which the media relay expects to receive audio/video from the caller telephone, to the caller telephone 12 in a message. The caller telephone replies to the call controller with an IP address at which it would like to receive audio/video and the call controller conveys that IP address to the media relay. The call may then be conducted between the caller and callee through the media relay and gateway.

Referring back to FIG. 1, if the call controller 14 receives a routing message of the type shown in FIG. 32, and which has at least one call forwarding number and/or a voicemail number, the call controller attempts to establish a call to the callee telephone 15 by seeking from the callee telephone a message indicating an IP address to which the media relay should send audio/video. If no such message is received from the callee telephone, no call is established. If no call is established within a pre-determined time, the call controller 14 attempts to establish a call with the next user identified in the call routing message in the same manner. This process is repeated until all call forwarding possibilities have been exhausted, in which case the call controller communicates with the voicemail server 19 identified in the routing message to obtain an IP address to which the media relay should send audio/video and the remainder of the process mentioned above for establishing IP addresses at the media relay 9 and the caller telephone is carried out to establish audio/video paths to allowing the caller to leave a voicemail message with the voicemail server.

When an audio/video path through the media relay is established, a call timer maintained by the call controller 14 logs the start date and time of the call and logs the call ID and an identification of the route (i.e., audio/video path IP address) for later use in billing.

Time to Live

Figure 33A:
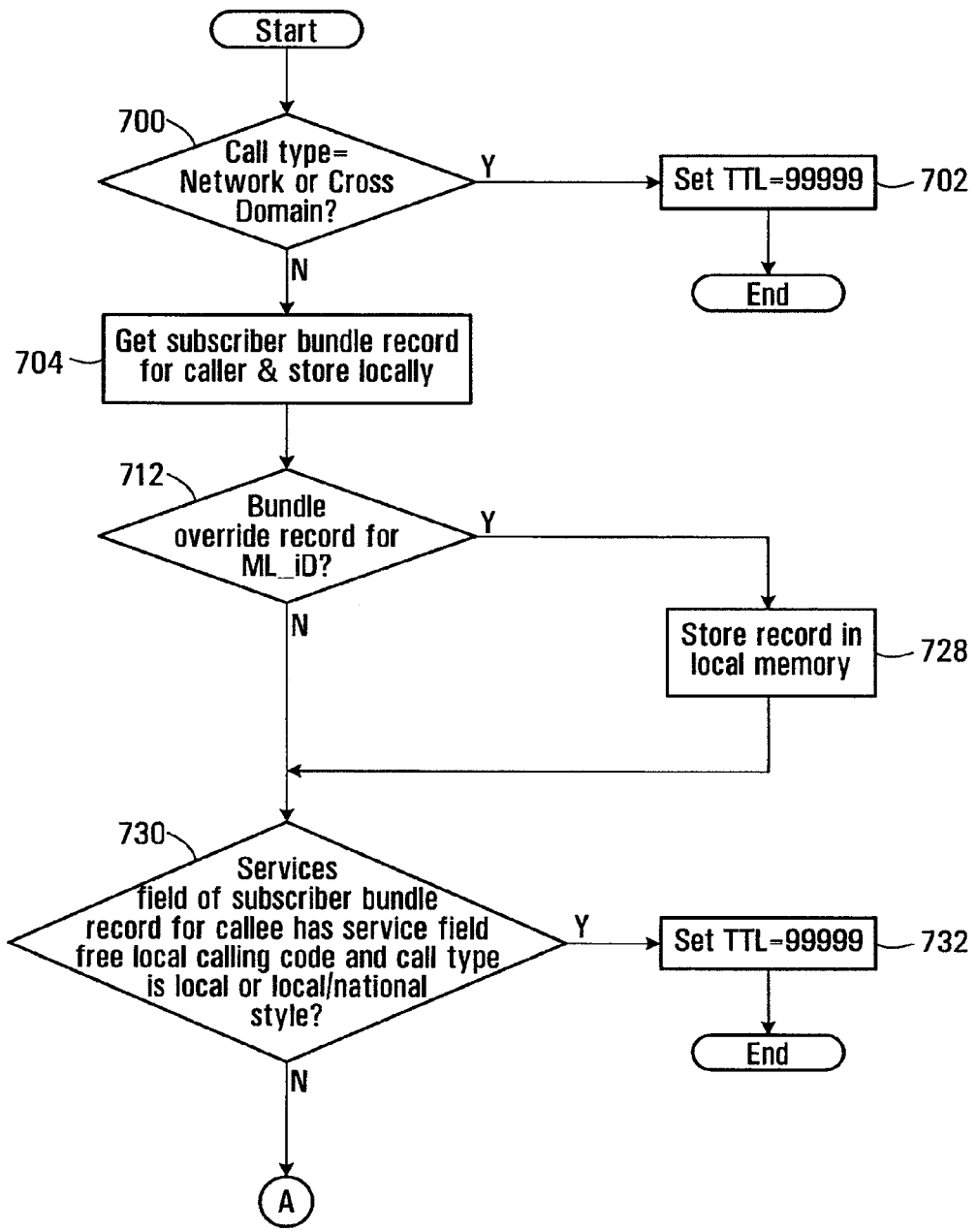
FIGS. 33A and 33B are respective portions of a flowchart of a process executed by the RC processor for determining a time to live value.
Figure 33B:
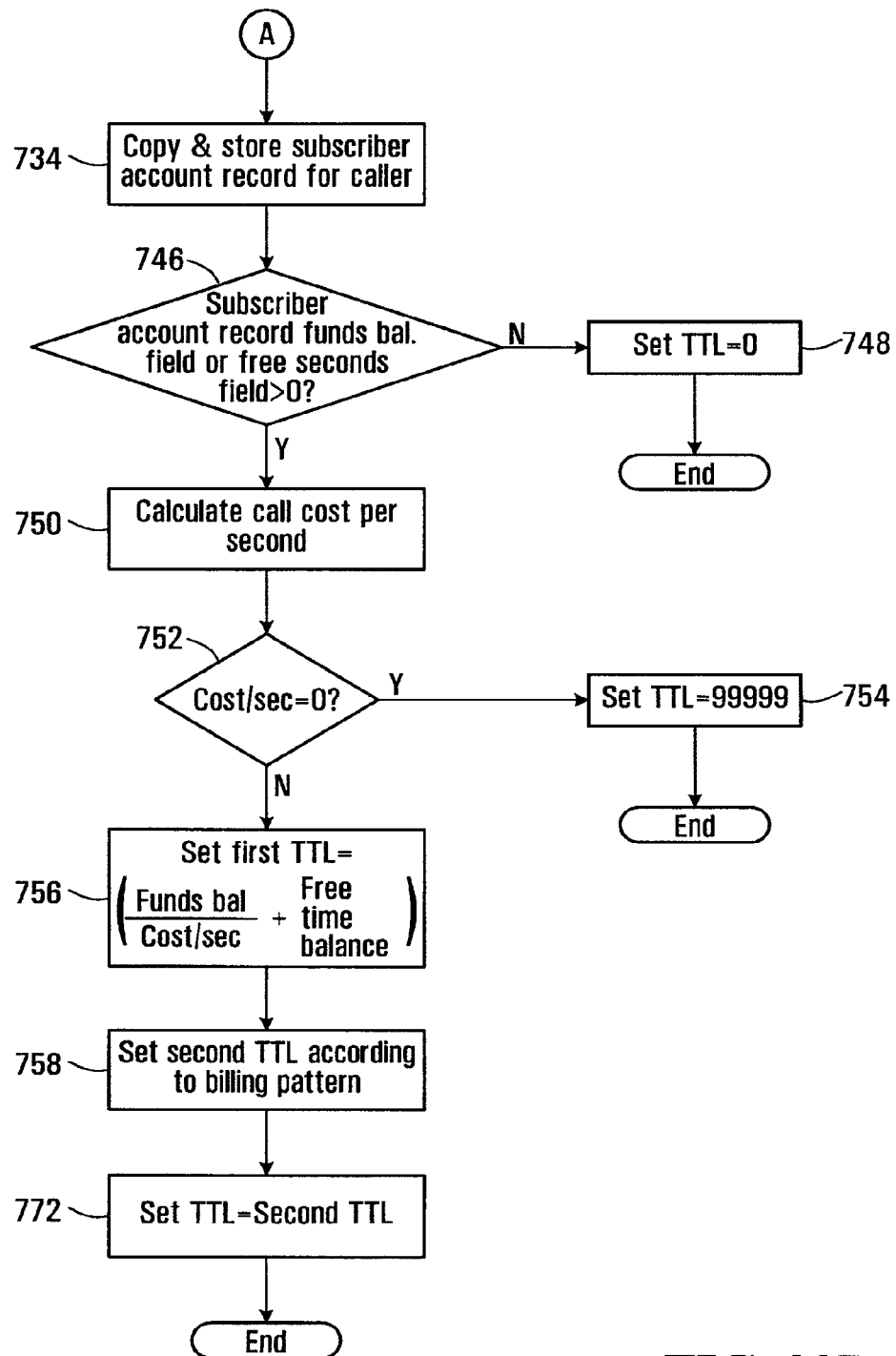

Referring to FIGS. 33A and 33B, a process for determining a time to live value for any of blocks 642 in FIG. 8C, 350 in FIG. 8A or 564 in FIG. 8D above is described. The process is executed by the processor 202 shown in FIG. 7. Generally, the process involves calculating a cost per unit time, calculating a first time value as a sum of a free time attributed to a participant in the communication session and the quotient of a funds balance held by the participant to the cost per unit time value and producing a second time value in response to the first time value and a billing pattern associated with the participant, the billing pattern including first and second billing intervals and the second time value being the time to permit a communication session to be conducted.

Referring to FIG. 33A, in this embodiment, the process begins with a first block 700 that directs the RC processor to determine whether or not the call type set at block 302 in FIG. 8A indicates the call is a network or cross-domain call. If the call is a network or cross-domain call, block 702 of FIG. 33A directs the RC processor to set the time to live equal to 99999 and the process is ended. Thus, the network or cross-domain call type has a long time to live. If at block 700 the call type is determined not to be a network or cross-domain type, block 704 directs the RC processor to get a subscriber bundle table record from the database 18 in FIG. 1 and store it locally in the subscriber bundle record buffer at the RC 14.

Referring to FIG. 34, a subscriber bundle table record is shown generally at 706. The record includes a user name field 708 and a services field 710. The user name field 708 holds a code identifying the subscriber user name and the services field 710 holds codes identifying service features assigned to the subscriber, such as free local calling, call blocking and voicemail, for example.

FIG. 35 shows an exemplary subscriber bundle record for the Vancouver caller. In this record the user name field 708 is loaded with the user name 2001 1050 8667 and the services field 710 is loaded with codes 10, 14 and 16 corresponding to free local calling, call blocking and voicemail, respectively. Thus, user 2001 1050 8667 has free local calling, call blocking and voicemail features.

Referring back to FIG. 33A, after having loaded a subscriber bundle record into the subscriber bundle record buffer, block 712 directs the RC processor to search the database (18) determine whether or not there is a bundle override table record for the master list ID value that was determined at block 410 in FIG. 8B. An exemplary bundle override table record is shown at 714 in FIG. 36. The bundle table record includes a master list ID field 716, an override type field 718, an override value field 720 a first interval field 722 and a second interval field 724. The master list ID field 716 holds a master list ID code. The override type field 718 holds an override type code indicating a fixed, percent or cent amount to indicate the amount by which a fee will be increased. The override value field 720 holds a real number representing the value of the override type. The first interval field 722 holds a value indicating the minimum number of seconds for a first level of charging and the second interval field 724 holds a number representing a second level of charging.

Referring to FIG. 37, a bundle override record for the located master list ID code is shown generally at 726 and includes a master list ID field 716 holding the code 1019 which was the code located in block 410 of FIG. 8B. The override type field 718 includes a code indicating the override type is a percentage value and the override value field 720 holds the value 10.0 indicating that the override will be 10.0% of the charged value. The first interval field 722 holds a value representing 30 seconds and the second interval field 724 holds a value representing 6 seconds. The 30 second value in the first interval field 722 indicates that charges for the route will be made at a first rate for 30 seconds and thereafter the charges will be made at a different rate in increments of 6 seconds, as indicated by the contents of the second interval field 724.

Referring back to FIG. 33A, if at block 712 the processor finds a bundle override record of the type shown in FIG. 37, block 728 directs the processor to store the bundle override record in local memory. In the embodiment shown, the bundle override record shown in FIG. 37 is stored in the bundle override record buffer at the RC as shown in FIG. 7. Still referring to FIG. 33A, block 730 then directs the RC processor to determine whether or not the subscriber bundle table record 706 in FIG. 35 has a services field including a code identifying that the user is entitled to free local calling and also directs the processor to determine whether or not the call type is not a cross domain cell, i.e. it is a local or local/national style. If both of these conditions are satisfied, block 732 directs the processor to set the time to live equal to 99999, giving the user a long period of time for the call. The process is then ended. If the conditions associated with block 730 are not satisfied, block 734 of FIG. 33B directs the RC processor to retrieve a subscriber account record associated with a participant in the call. This is done by copying and storing in the subscriber account record buffer a subscriber account record for the caller.

Referring to FIG. 38, an exemplary subscriber account table record is shown generally at 736. The record includes a user name field 738, a funds balance field 740 and a free time field 742. The user name field 738 holds a subscriber user name, the funds balance field 740 holds a real number representing the dollar value of credit available to the subscriber and the free time field 742 holds an integer representing the number of free seconds that the user is entitled to.

An exemplary subscriber account record for the Vancouver caller is shown generally at 744 in FIG. 39, wherein the user name field 738 holds the user name 2001 1050 8667, the funds balance field 740 holds the value $10.00, and the free time field 742 holds the value 100. The funds balance field holding the value of $10.00 indicates the user has $10.00 worth of credit and the free time field having the value of 100 indicates that the user has a balance of 100 free seconds of call time.

Referring back to FIG. 33B, after copying and storing the subscriber account record shown in FIG. 39 from the database to the subscriber account record buffer RC, block 746 directs the processor to determine whether or not the subscriber account record funds balance field 740 or free time field 742 are greater than zero. If they are not greater than zero, block 748 directs the processor to set the time to live equal to zero and the process is ended. The RC then sends a message back to the call controller to cause the call controller to deny the call to the caller. If the conditions associated with block 746 are satisfied, block 750 directs the processor to calculate the call cost per unit time. A procedure for calculating the call cost per unit time is described below in connection with FIG. 41.

Assuming the procedure for calculating the cost per second returns a number representing the call cost per second, block 752 directs the processor 202 in FIG. 7 to determine whether or not the cost per second is equal to zero. If so, block 754 directs the processor to set the time to live to 99999 to give the caller a very long length of call and the process is ended.

If at block 752 the call cost per second is not equal to zero, block 756 directs the processor 202 in FIG. 7 to calculate a first time to live value as a sum of a free time attributed to the participant in the communication session and the quotient of the funds balance held by the participant to the cost per unit time value. To do this, the processor 202 of FIG. 7 is directed to set a first time value or temporary time to live value equal to the sum of the free time provided in the free time field 742 of the subscriber account record shown in FIG. 39 and the quotient of the contents of the funds balance field 740 in the subscriber account record for the call shown in FIG. 39 and the cost per second determined at block 750 of FIG. 33B. Thus, for example, if at block 750 the cost per second is determined to be three cents per second and the funds balance field holds the value $10.00, the quotient of the funds balance and cost per second is 333 seconds and this is added to the contents of the free time field 742, which is 100, resulting in a time to live of 433 seconds.

Block 758 then directs the RC processor to produce a second time value in response to the first time value and the billing pattern associated with the participant as established by the bundle override record shown in FIG. 37. This process is shown in greater detail at 760 in FIG. 40 and generally involves producing a remainder value representing a portion of the second billing interval remaining after dividing the second billing interval into a difference between the first time value and the first billing interval.

Figure 40:
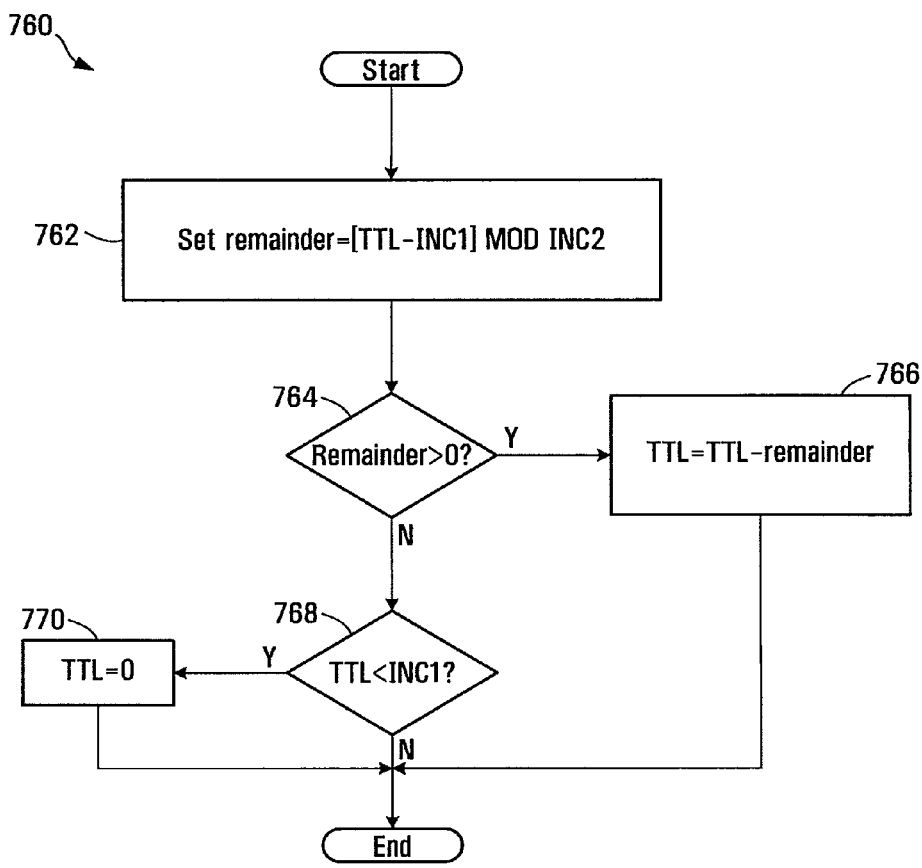
FIG. 40 is a flowchart of a process for producing a second time value executed by the RC processor circuit shown in FIG. 7.

Referring to FIG. 40, the process for producing the second time value begins with a first block 762 that directs the processor 202 in FIG. 7 to set a remainder value equal to the difference between the time to live value calculated at block 756 in FIG. 33B and the contents of the first interval field 722 of the record shown in FIG. 37, multiplied by the modulus of the contents of the second interval field 724 of FIG. 37. Thus, in the example given, the difference between the time to live field and the first interval field is 433 minus 30, which is 403 and therefore the remainder produced by the mod of 403 divided by 6 is 0.17. Block 764 then directs the processor to determine whether or not this remainder value is greater than zero and, if so, block 766 directs the processor to subtract the remainder from the first time value and set the difference as the second time value. To do this the processor is directed to set the time to live value equal to the current time to live of 403 minus the remainder of 1, i.e., 402 seconds. The processor is then returned back to block 758 of FIG. 33B.

Referring back to FIG. 40, if at block 764 the remainder is not greater than zero, block 768 directs the processor 202 of FIG. 7 to determine whether or not the time to live is less than the contents of the first interval field 722 in the record shown in FIG. 37. If so, then block 770 of FIG. 40 directs the processor to set the time to live equal to zero. Thus, the second time value is set to zero when the remainder is greater than zero and the first time value is less than the free time associated with the participant in the call. If at block 768 the conditions of that block are not satisfied, the processor returns the first time to live value as the second time to live value.

Thus, referring to FIG. 33B, after having produced a second time to live value, block 772 directs the processor to set the time to live value for use in blocks 342, 350 or 564.

Cost per Second

Referring back to FIG. 33B, at block 750 it was explained that a call cost per unit time is calculated. The following explains how that call cost per unit time value is calculated.

Figure 41:
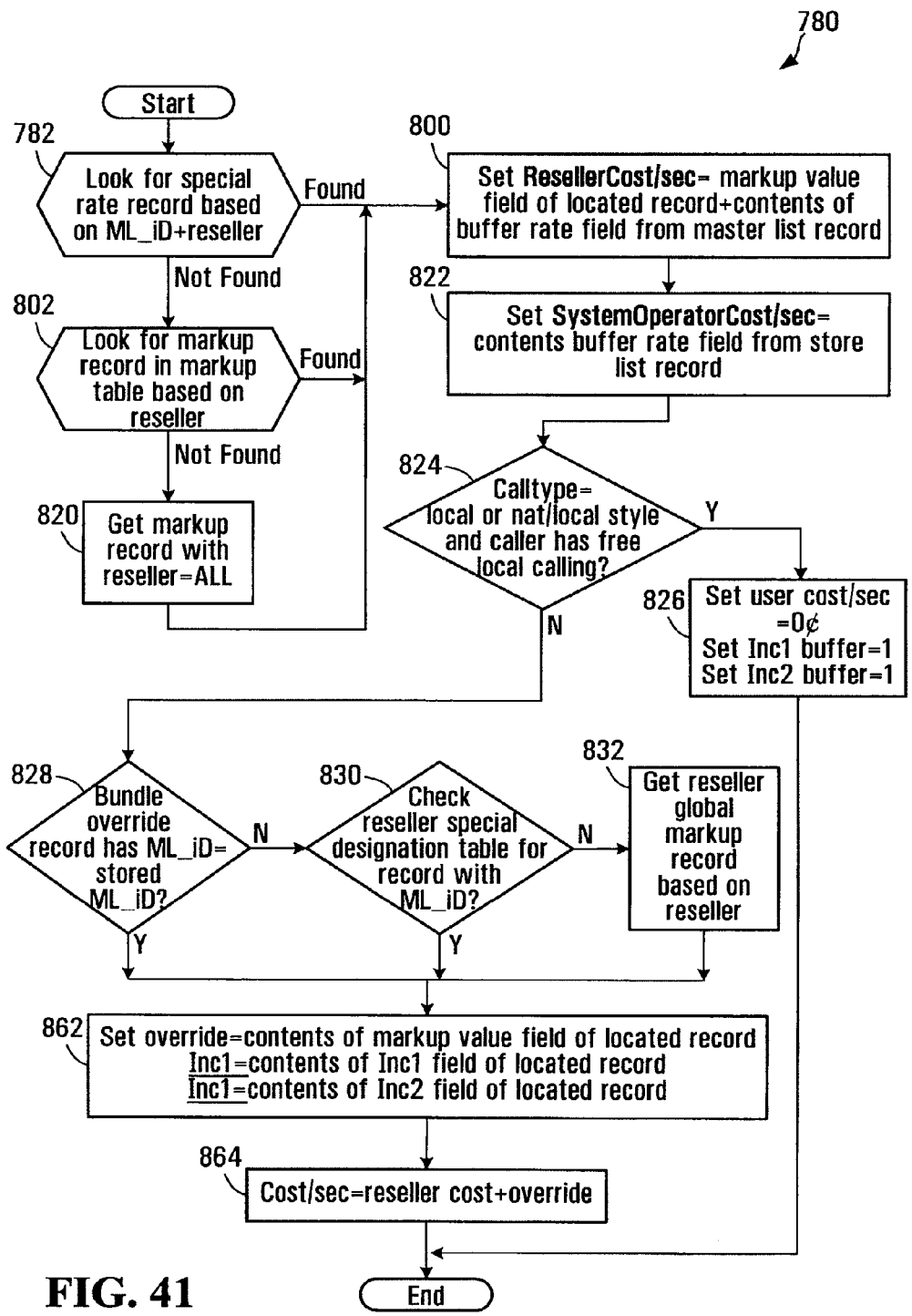
FIG. 41 is a flowchart for calculating a call cost per unit time.

Referring to FIG. 41, a process for calculating a cost per unit time is shown generally at 780. The process is executed by the processor 202 in FIG. 7 and generally involves locating a record in a database, the record comprising a markup type indicator, a markup value and a billing pattern and setting a reseller rate equal to the sum of the markup value and the buffer rate, locating at least one of an override record specifying a route cost per unit time amount associated with a route associated with the communication session, a reseller record associated with a reseller of the communications session, the reseller record specifying a reseller cost per unit time associated with the reseller for the communication session and a default operator markup record specifying a default cost per unit time and setting as the cost per unit time the sum of the reseller rate and at least one of the route cost per unit time, the reseller cost per unit time and the default cost per unit time.

The process begins with a first set of blocks 782, 802 and 820 which direct the processor 202 in FIG. 7 to locate at least one of a record associated with a reseller and a route associated with the reseller, a record associated with the reseller, and a default reseller mark-up record. Block 782, in particular, directs the processor to address the database 18 to look for a record associated with a reseller and a route with the reseller by looking for a special rate record based on the master list ID established at block 410 in FIG. 8C.

Referring to FIG. 42, a system operator special rate table record is shown generally at 784. The record includes a reseller field 786, a master list ID field 788, a mark-up type field 790, a mark-up value field 792, a first interval field 794 and a second interval field 796. The reseller field 786 holds a reseller ID code and the master list ID field 788 holds a master list ID code. The mark-up type field 790 holds a mark-up type such as fixed percent or cents and the mark-up value field 792 holds a real number representing the value corresponding to the mark-up type. The first interval field 794 holds a number representing a first level of charging and the second interval field 796 holds a number representing a second level of charging.

An exemplary system operator special rate table for a reseller known as "Klondike" is shown at 798 in FIG. 43. In this record, the reseller field 786 holds a code indicating the retailer ID is Klondike, the master list ID field 788 holds the code 1019 to associate the record with the master list ID code 1019. The mark-up type field 790 holds a code indicating the mark-up type is cents and the mark-up value field 792 holds a mark-up value indicating $\frac{1}{10}$ of one cent. The first interval field 794 holds the value 30 and the second interval field 796 holds the value 6, these two fields indicating that the operator allows 30 seconds for free and then billing is done in increments of 6 seconds after that.

Referring back to FIG. 41, if at block 782 a record such as the one shown in FIG. 43 is located in the system operator special rates table, the processor is directed to block 800 in FIG. 41. If such a record is not found in the system operator special rates table, block 802 directs the processor to address the database 18 to look in a system operator mark-up table for a mark-up record associated with the reseller.

Referring to FIG. 44, an exemplary system operator mark-up table record is shown generally at 804. The record includes a reseller field 806, a mark-up type field 808, a mark-up value field 810, a first interval field 812 and a second interval field 814. The reseller mark-up type, mark-up value, first interval and second interval fields are as described in connection with the fields by the same names in the system operator special rates table shown in FIG. 42.

FIG. 45 provides an exemplary system operator mark-up table record for the reseller known as Klondike and therefore the reseller field 806 holds the value "Klondike", the mark-up type field 808 holds the value cents, the markup value field holds the value 0.01, the first interval field 812 holds the value 30 and the second interval field 814 holds the value 6. This indicates that the reseller "Klondike" charges by the cent at a rate of one cent per minute. The first 30 seconds of the call are free and billing is charged at the rate of one cent per minute in increments of 6 seconds.

FIG. 46 provides an exemplary system operator mark-up table record for cases where no specific system operator mark-up table record exists for a particular reseller, i.e., a default reseller mark-up record. This record is similar to the record shown in FIG. 45 and the reseller field 806 holds the value "all", the mark-up type field 808 is loaded with a code indicating mark-up is based on a percentage, the mark-up value field 810 holds the percentage by which the cost is marked up, and the first and second interval fields 812 and 814 identify first and second billing levels.

Referring back to FIG. 41, if at block 802 a specific mark-up record for the reseller identified at block 782 is not located, block 820 directs the processor to get the mark-up record shown in FIG. 46, having the "all" code in the reseller field 806. The processor is then directed to block 800.

Referring back to FIG. 41, at block 800, the processor 202 of FIG. 7 is directed to set a reseller rate equal to the sum of the mark-up value of the record located by blocks 782, 802 or 820 and the buffer rate specified by the contents of the buffer rate field 516 of the master list record shown in FIG. 20. To do this, the RC processor sets a variable entitled "reseller cost per second" to a value equal to the sum of the contents of the mark-up value field (792, 810) of the associated record, plus the contents of the buffer rate field (516) from the master list record associated with the master list ID. Then, block 822 directs the processor to set a system operator cost per second variable equal to the contents of the buffer rate field (516) from the master list record. Block 824 then directs the processor to determine whether the call type flag indicates the call is local or national/local style and whether the caller has free local calling. If both these conditions are met, then block 826 sets the user cost per second variable equal to zero and sets two increment variables equal to one, for use in later processing. The cost per second has thus be calculated and the process shown in FIG. 41 is ended.

If at block 824 the conditions of that block are not met, the processor 202 of FIG. 7 is directed to locate at least one of a bundle override table record specifying a route cost per unit time associated with a route associated with the communication session, a reseller special destinations table record associated with a reseller of the communications session, the reseller record specifying a reseller cost per unit time associated with the reseller for the communication session and a default reseller global markup record specifying a default cost per unit time.

To do this block 828 directs the processor 202 of FIG. 7 to determine whether or not the bundle override record 726 in FIG. 37 located at block 712 in FIG. 33A has a master list ID equal to the stored master list ID that was determined at block 410 in FIG. 8B. If not, block 830 directs the processor to find a reseller special destinations table record in a reseller special destinations table in the database (18), having a master list ID code equal to the master list ID code of the master list ID that was determined at block 410 in FIG. 8B. An exemplary reseller special destinations table record is shown in FIG. 47 at 832. The reseller special destinations table record includes a reseller field 834, a master list ID field 836, a mark-up type field 838, a mark-up value field 840, a first interval field 842 and a second interval field 844. This record has the same format as the system operator special rates table record shown in FIG. 42, but is stored in a different table to allow for different mark-up types and values and time intervals to be set according to resellers' preferences. Thus, for example, an exemplary reseller special destinations table record for the reseller "Klondike" is shown at 846 in FIG. 48. The reseller field 834 holds a value indicating the reseller as the reseller "Klondike" and the master list ID field holds the code 1019. The markup type field 838 holds a code indicating the mark-up type is percent and the mark-up value field 840 holds a number representing the mark-up value as 5%. The first and second interval fields identify different billing levels used as described earlier.

Referring back to FIG. 41, the record shown in FIG. 48 may be located at block 830, for example. If at block 830 such a record is not found, then block 832 directs the processor to get a default operator global mark-up record based on the reseller ID.

Referring to FIG. 49, an exemplary default reseller global mark-up table record is shown generally at 848. This record includes a reseller field 850, a mark-up type field 852, a mark-up value field 854, a first interval field 856 and a second interval field 858. The reseller field 850 holds a code identifying the reseller. The mark-up type field 852, the mark-up value field 854 and the first and second interval fields 856 and 858 are of the same type as described in connection with fields of the same name in FIG. 47, for example. The contents of the fields of this record 860 may be set according to system operator preferences, for example.

Referring to FIG. 50, an exemplary reseller global mark-up table record is shown generally at 860. In this record, the reseller field 850 holds a code indicating the reseller is "Klondike", the mark-up type field 852 holds a code indicating the mark-up type is percent, the mark-up value field 854 holds a value representing 10% as the mark-up value, the first interval field 856 holds the value 30 and the second interval field 858 holds the values 30 and 6 respectively to indicate the first 30 seconds are free and billing is to be done in 6 second increments after that.

Referring back to FIG. 41, should the processor get to block 832, the reseller global mark-up table record as shown in FIG. 50 is retrieved from the database and stored locally at the RC. As seen in FIG. 41, it will be appreciated that if the conditions are met in blocks 828 or 830, or if the processor executes block 832, the processor is then directed to block 862 which causes it to set an override value equal to the contents of the mark-up value field of the located record, to set the first increment variable equal to the contents of the first interval field of the located record and to set the second increment variable equal to the contents of the second interval field of the located record. (The increment variables were alternatively set to specific values at block 826 in FIG. 41.)

It will be appreciated that the located record could be a bundle override record of the type shown in FIG. 37 or the located record could be a reseller special destination record of the type shown in FIG. 48 or the record could be a reseller global mark-up table record of the type shown in FIG. 50. After the override and first and second increment variables have been set at block 862, the processor 202 if FIG. 7 is directed to set as the cost per unit time the sum of the reseller rate and at least one of the route cost per unit time, the reseller cost per unit time and the default cost per unit time, depending on which record was located. To do this, block 864 directs the processor to set the cost per unit time equal to the sum of the reseller cost set at block 800 in FIG. 41, plus the contents of the override variable calculated in block 862 in FIG. 41. The cost per unit time has thus been calculated and it is this cost per unit time that is used in block 752 of FIG. 33B, for example.

Terminating the Call

In the event that either the caller or the callee terminates a call, the telephone of the terminating party sends a SIP bye message to the controller 14. An exemplary SIP bye message is shown at 900 in FIG. 51 and includes a caller field 902, a callee field 904 and a call ID field 906. The caller field 902 holds a twelve digit user name, the callee field 904 holds a PSTN compatible number or user name, and the call ID field 906 holds a unique call identifier field of the type shown in the call ID field 65 of the SIP invite message shown in FIG. 3.

Thus, for example, referring to FIG. 52, a SIP bye message for the Calgary callee is shown generally at 908 and the caller field 902 holds a user name identifying the caller, in this case 2001 1050 8667, the callee field 904 holds a user name identifying the Calgary callee, in this case 2001 1050 2222, and the call ID field 906 holds the code FA10@192.168.0.20, which is the call ID for the call.

Figure 53:
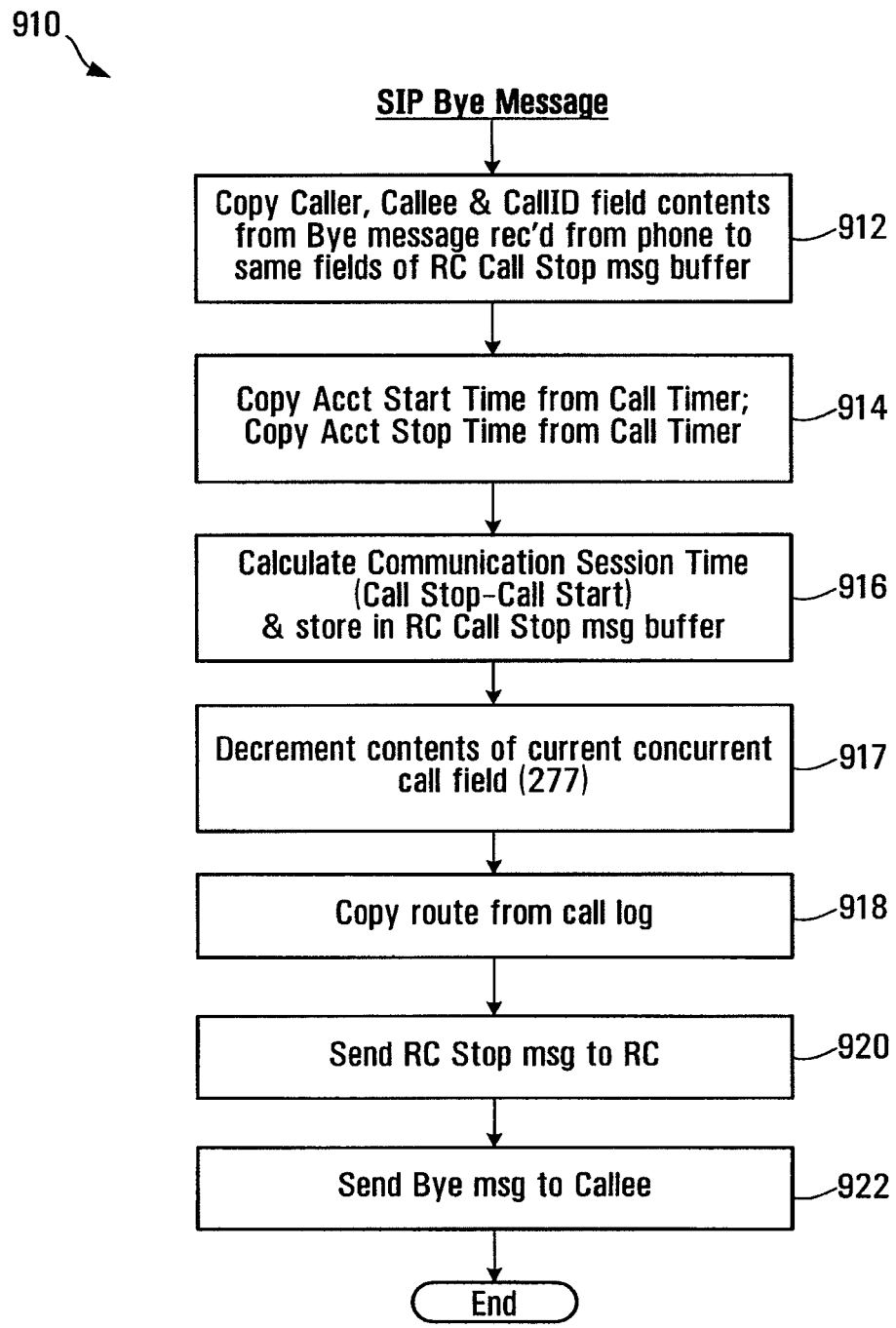
FIG. 53 is a flowchart of a process executed by the call controller for producing a RC stop message in response to receipt of a SIP bye message.

The SIP bye message shown in FIG. 52 is received at the call controller 14 and the call controller executes a process as shown generally at 910 in FIG. 53. The process includes a first block 912 that directs the call controller processor 202 of FIG. 7 to copy the caller, callee and call ID field contents from the SIP bye message received from the terminating party to corresponding fields of an RC stop message buffer (not shown). Block 914 then directs the processor to copy the call start time from the call timer and to obtain a call stop time from the call timer. Block 916 then directs the call controller to calculate a communication session time by determining the difference in time between the call start time and the call stop time. This session time is then stored in a corresponding field of the RC call stop message buffer. Block 917 then directs the processor to decrement the contents of the current concurrent call field 277 of the dialing profile for the caller as shown in FIG. 10, to indicate that there is one less concurrent call in progress. A copy of the amended dialing profile for the caller is then stored in the database 18 of FIG. 1. Block 918 then directs the processor to copy the route from the call log. An RC call stop message produced as described above is shown generally at 1000 in FIG. 54. An RC call stop message specifically associated with the call made to the Calgary callee is shown generally at 1020 in FIG. 55.

Referring to FIG. 54, the RC stop call message includes a caller field 1002, callee field 1004, a call ID field 1006, an account start time field 1008, an account stop time field 1010, a communication session time 1012 and a route field 1014. The caller field 1002 holds a username, the callee field 1004 holds a PSTN-compatible number or system number, the call ID field 1006 hold the unique call identifier received from the SIP invite message shown in FIG. 3, the account start time field 1008 holds the date and start time of the call, the account stop time field 1010 holds the date and time the call ended, the communication session time field 1012 holds a value representing the difference between the start time and the stop time, in seconds, and the route field 1014 holds the IP address for the communications link that was established.

Referring to FIG. 55, an exemplary RC stop call message for the Calgary callee is shown generally at 1020. In this example the caller field 1002 holds the user name 2001 1050 8667 identifying the Vancouver-based caller and the callee field 1004 holds the user name 2001 1050 2222 identifying the Calgary callee. The contents of the call ID field 1006 are FA10@192.168.0.20. The contents of the account start time field 1008 are Dec. 30, 2006 12:12:12 and the contents of the account stop time field are Dec. 30, 2006 12:12:14. The contents of the communication session time field 1012 are 2 to indicate 2 seconds call duration and the contents of the route field are 72.64.39.58.

Referring back to FIG. 53, after having produced an RC call stop message, block 920 directs the processor 202 in FIG. 7 to send the RC stop message compiled in the RC call stop message buffer to the RC 16 of FIG. 1. Block 922 directs the call controller 14 to send a "bye" message back to the party that did not terminate the call.

Figure 56A:
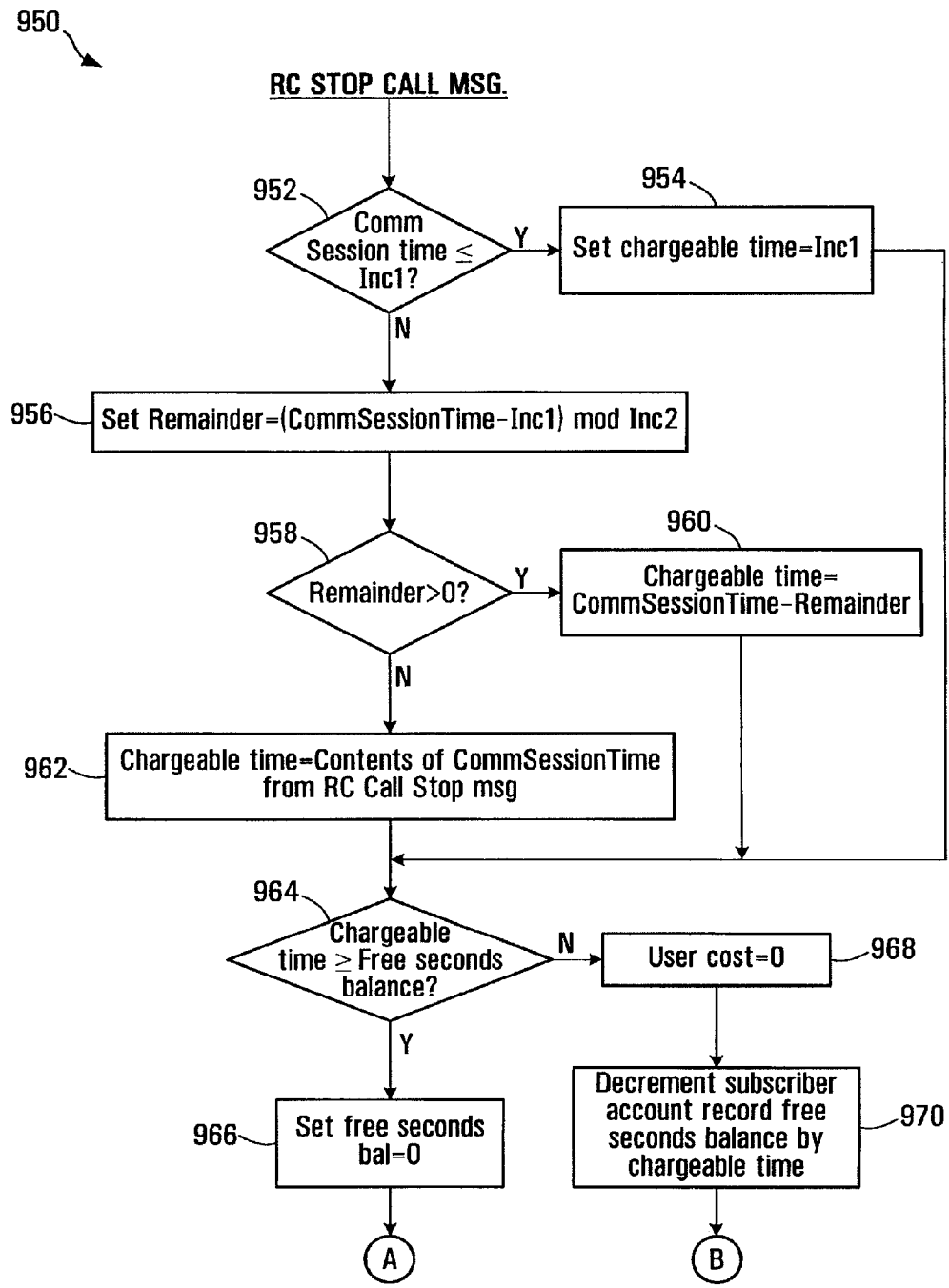
FIGS. 56A and 56B are respective portions of a flowchart of a RC call stop message handling routine executed by the RC shown in FIG. 1.
Figure 56B:
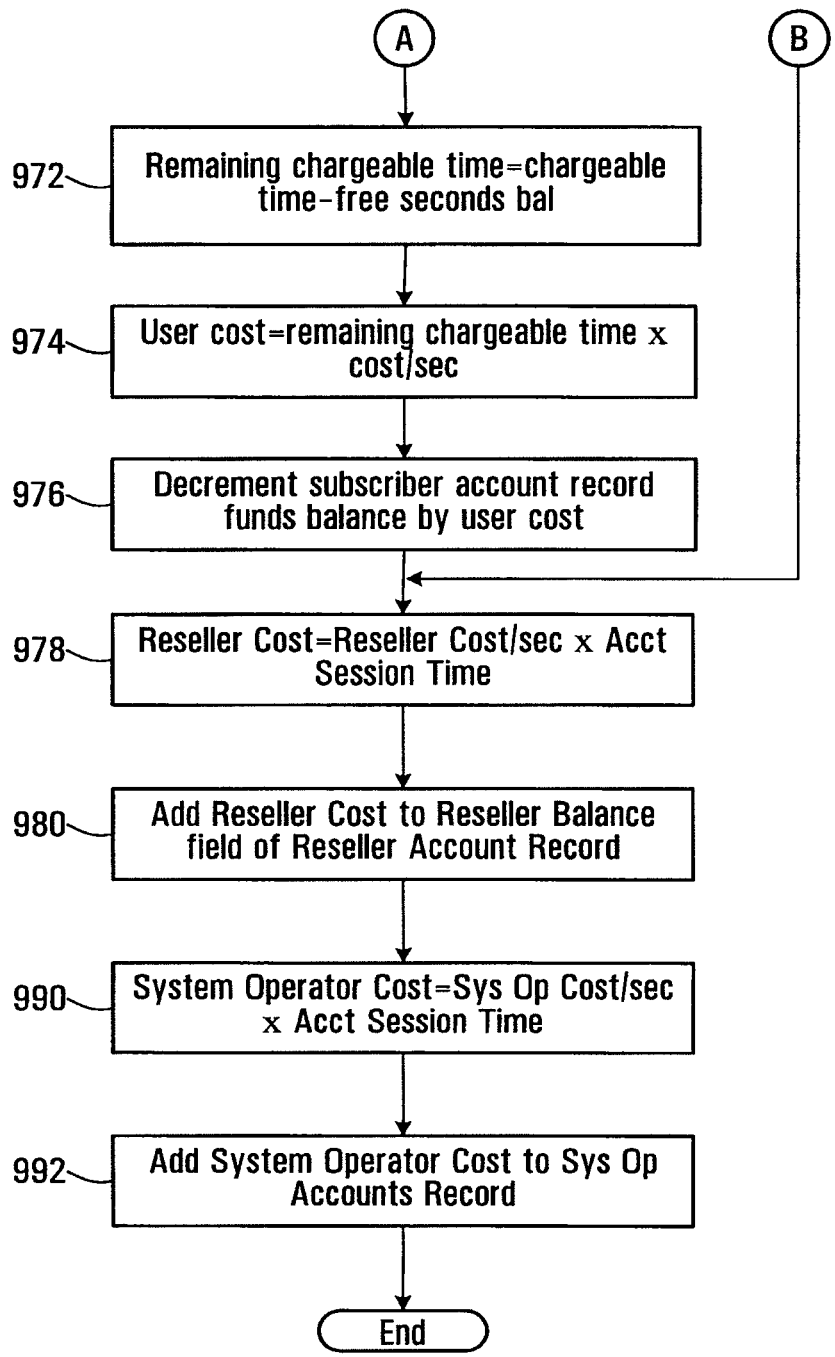

The RC 16 of FIG. 1 receives the call stop message and an RC call stop message process is invoked at the RC, the process being shown at 950 in FIGS. 56A, 56B and 56C. Referring to FIG. 56A, the RC stop message process 950 begins with a first block 952 that directs the processor 202 in FIG. 7 to determine whether or not the communication session time is less than or equal to the first increment value set by the cost calculation routine shown in FIG. 41, specifically blocks 826 or 862 thereof. If this condition is met, then block 954 of FIG. 56A directs the RC processor to set a chargeable time variable equal to the first increment value set at block 826 or 862 of FIG. 41. If at block 952 of FIG. 56A the condition is not met, block 956 directs the RC processor to set a remainder variable equal to the difference between the communication session time and the first increment value mod the second increment value produced at block 826 or 862 of FIG. 41. Then, the processor is directed to block 958 of FIG. 56A which directs it to determine whether or not the remainder is greater than zero. If so, block 960 directs the RC processor to set the chargeable time variable equal to the difference between the communication session time and the remainder value. If at block 958 the remainder is not greater than zero, block 962 directs the RC processor to set the chargeable time variable equal to the contents of the communication session time from the RC stop message. The processor is then directed to block 964. In addition, after executing block 954 or block 960, the processor is directed to block 964.

Block 964 directs the processor 202 of FIG. 7 to determine whether or not the chargeable time variable is greater than or equal to the free time balance as determined from the free time field 742 of the subscriber account record shown in FIG. 39. If this condition is satisfied, block 966 of FIG. 56A directs the processor to set the free time field 742 in the record shown in FIG. 39, to zero. If the chargeable time variable is not greater than or equal to the free time balance, block 968 directs the RC processor to set a user cost variable to zero and Block 970 then decrements the free time field 742 of the subscriber account record for the caller by the chargeable time amount determined by block 954, 960 or 962.

If at Block 964 the processor 202 of FIG. 7 was directed to Block 966 which causes the free time field (742 of FIG. 39) to be set to zero, referring to FIG. 56B, Block 972 directs the processor to set a remaining chargeable time variable equal to the difference between the chargeable time and the contents of the free time field (742 of FIG. 39). Block 974 then directs the processor to set the user cost variable equal to the product of the remaining chargeable time and the cost per second calculated at Block 750 in FIG. 33B. Block 976 then directs the processor to decrement the funds balance field (740) of the subscriber account record shown in FIG. 39 by the contents of the user cost variable calculated at Block 974.

After completing Block 976 or after completing Block 970 in FIG. 56A, block 978 of FIG. 56B directs the processor 202 of FIG. 7 to calculate a reseller cost variable as the product of the reseller rate as indicated in the mark-up value field 810 of the system operator mark-up table record shown in FIG. 45 and the communication session time determined at Block 916 in FIG. 53. Then, Block 980 of FIG. 56B directs the processor to add the reseller cost to the reseller balance field 986 of a reseller account record of the type shown in FIG. 57 at 982.

The reseller account record includes a reseller ID field 984 and the aforementioned reseller balance field 986. The reseller ID field 984 holds a reseller ID code, and the reseller balance field 986 holds an accumulated balance of charges.

Referring to FIG. 58, a specific reseller accounts record for the reseller "Klondike" is shown generally at 988. In this record the reseller ID field 984 holds a code representing the reseller "Klondike" and the reseller balance field 986 holds a balance of $100.02. Thus, the contents of the reseller balance field 986 in FIG. 58 are incremented by the reseller cost calculated at block 978 of FIG. 56B.

Still referring to FIG. 56B, after adding the reseller cost to the reseller balance field as indicated by Block 980, Block 990 directs the processor to 202 of FIG. 7 calculate a system operator cost as the product of the system operator cost per second, as set at block 822 in FIG. 41, and the communication session time as determined at Block 916 in FIG. 53. Block 992 then directs the processor to add the system operator cost value calculated at Block 990 to a system operator accounts table record of the type shown at 994 in FIG. 59. This record includes a system operator balance field 996 holding an accumulated charges balance. Referring to FIG. 60 in the embodiment described, the system operator balance field 996 may hold the value $1,000.02 for example, and to this value the system operator cost calculated at Block 990 is added when the processor executes Block 992 of FIG. 56B.

Ultimately, the final reseller balance 986 in FIG. 58 holds a number representing an amount owed to the reseller by the system operator and the system operator balance 996 of FIG. 59 holds a number representing an amount of profit for the system operator.

While specific embodiments of the invention have been described and illustrated, such embodiments should be considered illustrative of the invention only and not as limiting the invention as construed in accordance with the accompanying claims.

What is claimed is:

1. A computer implemented process for attributing charges for communications services, the process comprising:
    causing a processor to determine a first chargeable time in response to a communication session time and a pre-defined billing pattern;
    causing the processor to determine a user cost value in response to the first chargeable time and a free time value associated with a user of the communications services;
    causing the processor to change an account balance associated with the user in response to the user cost value;
    causing the processor to change an account balance associated with a reseller of the communications services in response to a reseller cost per unit time and the communication session time; and
    causing the processor to change an account balance associated with an operator of the communications services in response to an operator cost per unit time and the communication session time.

2. The process of claim 1, wherein determining the first chargeable time comprises:
    causing the processor to locate at least one of:
        an override record specifying a billing pattern associated with a route associated with the communication session;
        a reseller record associated with a reseller of the communications session, the reseller record specifying a billing pattern associated with the reseller for the communication session; and
        a default record specifying a billing pattern; and
        causing the processor to set as the pre-defined billing pattern the billing pattern of the located record, wherein the billing pattern of the located record comprises a first billing interval and a second billing interval.

3. The process of claim 2, wherein determining the first chargeable time comprises causing the processor to set the first chargeable time equal to the first billing interval when the communication session time is less than or equal to the first billing interval.

4. The process of claim 2, wherein determining the first chargeable time comprises causing the processor to produce a remainder value representing a portion of the second billing interval remaining after dividing the second billing interval into a difference between the communication session time and the first billing interval when the communication session time is greater than the communication session time; and setting the first chargeable time to a difference between the communication session time and the remainder when the remainder is greater than zero; and setting the first chargeable time to the communication session time when the remainder is not greater than zero.

5. The process of claim 4, further comprising causing the processor to set the free time value to zero when the first chargeable time is greater than or equal to the free time value.

6. The process of claim 4, further comprising causing the processor to set the user cost to zero when the first chargeable time is less than the free time value.

7. The process of claim 6, further comprising causing the processor to change a user free time balance in response to the first chargeable time.

8. The process of claim 5, further comprising causing the processor to determine a remaining chargeable time by determining a difference between the first chargeable time and the free time value.

9. The process of claim 8, wherein changing an account balance associated with the user comprises causing the processor to calculate the user cost value in response to the remaining chargeable time and a user cost per unit time.

10. The process of claim 9, further comprising causing the processor to change a user funds balance associated with the user in response to the user cost value.

11. The process of claim 1, further comprising determining the reseller cost per unit time by:

locating at least one route record specifying a buffer rate for use of a route used in providing the communications services;

locating a record associated with the reseller specifying a reseller markup rate; and determining the reseller cost per unit time in response to the buffer rate and the reseller markup rate.

12. The process of claim 11, further comprising determining the operator cost per unit time by setting the buffer rate as the operator cost per unit time.

13. A computer-implemented process for attributing charges for communications services, the process comprising initiating the process of claim 1, in response to termination of a communication session.

14. A non-transitory computer readable medium encoded with instructions for directing a processor circuit to execute the process of claim 1.

15. An apparatus for attributing charges for communications services, the apparatus comprising:

a processor operably configured to receive signals representing a communication session time, a pre-defined billing pattern, a free time value associated with a user of the communications services, a reseller cost per unit time; and an operator cost per unit time;

a non-transitory computer readable medium encoded with codes for directing the processor to:

receive the signals representing the communication session time, the pre-defined billing pattern, the free time value associated with a user of the communications services, the reseller cost per unit time, and the operator cost per unit time;

determine a first chargeable time in response to the communication session time and the pre-defined billing pattern;

determine a user cost value in response to the first chargeable time and the free time value;

cause an account balance associated with the user to be changed in response to the user cost value;

cause an account balance associated with a reseller of the communications services in response to the reseller cost per unit time and the communication session time; and cause an account balance associated with an operator of the communications services to be changed in response to the operator cost per unit time and the communication session time.

16. The apparatus of claim 15, wherein the codes include codes for directing the processor to determine the first chargeable time by:

causing the processor to locate at least one of:

an override record specifying a billing pattern associated with a route associated with the communication session;

a reseller record associated with a reseller of the communications session, the reseller record specifying a billing pattern associated with the reseller for the communication session; and a default record specifying a billing pattern; and causing the processor to set as the pre-defined billing pattern the billing pattern of the located record, wherein the billing pattern of the located record comprises a first billing interval and a second billing interval.

17. The apparatus of claim 16, wherein the codes for directing the processor to determine the first chargeable time comprise codes for causing the processor to set the first chargeable time equal to the first billing interval when the communication session time is less than or equal to the first billing interval.

18. The apparatus of claim 16, wherein the codes for directing the processor to determine the first chargeable time comprise codes for causing the processor to produce a remainder value representing a portion of the second billing interval remaining after dividing the second billing interval into a difference between the communication session time and the first billing interval when the communication session time is greater than the communication session time; and codes for causing the processor to set the first chargeable time to a difference between the communication session time and the remainder when the remainder is greater than zero; and codes for causing the processor to set the first chargeable time to the communication session time when the remainder is not greater than zero.

19. The apparatus of claim 18, wherein the codes for directing the processor further comprise codes for causing the processor to set the free time value to zero when the first chargeable time is greater than or equal to the free time value.

20. The apparatus of claim 18, wherein the codes for directing the processor further comprise codes for causing the processor to set the user cost to zero when the first chargeable time is less than the free time value.

21. The apparatus of claim 20, wherein the codes for directing the processor further comprise codes for causing the processor to change a user free time balance in response to the first chargeable time.

22. The apparatus of claim 19, wherein the codes for directing the processor further comprise codes for causing the processor to determine a remaining chargeable time by determining a difference between the first chargeable time and the free time value.

23. The apparatus of claim 22, wherein the codes for directing the processor to change an account balance associated with the user comprise codes for directing the processor to cause the processor to calculate the user cost value in response to the remaining chargeable time and a user cost per unit time.

24. The apparatus of claim 23, wherein the codes for directing the processor further comprise codes for causing the processor to change a user funds balance associated with the user in response to the user cost value.

25. The apparatus of claim 15, further comprising codes for directing the processor to determine the reseller cost per unit time by:
  locating at least one route record specifying a buffer rate for use of a route used in providing the communications services;
  locating a record associated with the reseller specifying a reseller markup rate; and
  determining the reseller cost per unit time in response to the buffer rate and the reseller markup rate.

26. The apparatus of claim 15, wherein the codes for directing the processor further comprise codes for causing the processor to determine the operator cost per unit time by setting the buffer rate as the operator cost per unit time.

27. The apparatus of claim 15, wherein the codes include codes for directing the processor to receive a signal indicating termination of a communication session.

28. An apparatus for attributing charges for communications services, the apparatus comprising:
  means for receiving signals representing a communication session time, a pre-defined billing pattern, a free time value associated with a user of the communications services, a reseller cost per unit time; and an operator cost per unit time;
  means for determining a first chargeable time in response to the communication session time and the pre-defined billing pattern;
  means for determining a user cost value in response to the first chargeable time and the free time value;
  means for causing an account balance associated with the user to be changed in response to the user cost value;
  means for causing an account balance associated with a reseller of the communications services in response to the reseller cost per unit time and the communication session time; and
  means for causing an account balance associated with an operator of the communications services to be changed in response to the operator cost per unit time and the communication session time.

29. The apparatus of claim 28, wherein the means for determining the first chargeable time includes:
  means for locating at least one of:
    an override record specifying a billing pattern associated with a route associated with the communication session;
    a reseller record associated with a reseller of the communications session, the reseller record specifying a billing pattern associated with the reseller for the communication session; and
    a default record specifying a billing pattern; and
  means for setting as the pre-defined billing pattern the billing pattern of the located record, wherein the billing pattern of the located record comprises a first billing interval and a second billing interval.

30. The apparatus of claim 28, wherein means for determining the first chargeable time includes means for setting the first chargeable time equal to the first billing interval when the communication session time is less than or equal to the first billing interval.

31. The apparatus of claim 28, wherein the means for determining the first chargeable time comprises means for producing a remainder value representing a portion of the second billing interval remaining after dividing the second billing interval into a difference between the communication session time and the first billing interval when the communication session time is greater than the communication session time; and further comprising
  means for setting the first chargeable time to a difference between the communication session time and the remainder when the remainder is greater than zero; and
  means for setting the first chargeable time to the communication session time when the remainder is not greater than zero.

32. The apparatus of claim 31 further comprising means for setting the free time value to zero when the first chargeable time is greater than or equal to the free time value.

33. The apparatus of claim 31, further comprising setting the user cost to zero when the first chargeable time is less than the free time value.

34. The apparatus of claim 33, further comprising means for changing a user free time balance in response to the first chargeable time.

35. The apparatus of claim 32, further comprising means for determining a remaining chargeable time by determining a difference between the first chargeable time and the free time value.

36. The apparatus of claim 35, wherein the means for changing an account balance associated with the user includes means for calculating the user cost value in response to the remaining chargeable time and a user cost per unit time.

37. The apparatus of claim 35, further comprising means for changing a user funds balance associated with the user in response to the user cost value.

38. The apparatus of claim 28, further comprising means for determining the reseller cost per unit time by:
  locating at least one route record specifying a buffer rate for use of a route used in providing the communications services;
  locating a record associated with the reseller specifying a reseller markup rate; and
  determining the reseller cost per unit time in response to the buffer rate and the reseller markup rate.

39. The apparatus of claim 38, further comprising means for determining the operator cost per unit time by setting the buffer rate as the operator cost per unit time.

40. The apparatus of claim 28, further comprising means for receiving a signal indicating termination of a communication session.

* * * * *